(12) United States Patent
Clawson et al.

(10) Patent No.: US 7,704,965 B2
(45) Date of Patent: Apr. 27, 2010

(54) METHODS AND MATERIALS FOR TREATING HUMAN PAPILLOMAVIRUS INFECTIONS

(75) Inventors: Gary A. Clawson, Bethesda, MD (US); Wei-Hua Pan, Hummelstown, PA (US); Diane Thiboutot, Hershey, PA (US); Neil Christensen, Harrisburg, PA (US)

(73) Assignee: The Penn State Research Foundation, University Park, PA (US)

( * ) Notice: Subject to any disclaimer, the term of this patent is extended or adjusted under 35 U.S.C. 154(b) by 954 days.

(21) Appl. No.: 10/519,122

(22) PCT Filed: Jun. 26, 2003

(86) PCT No.: PCT/US03/20340

§ 371 (c)(1), (2), (4) Date: Aug. 8, 2005

(87) PCT Pub. No.: WO2004/002416

PCT Pub. Date: Jan. 8, 2004

(65) Prior Publication Data

US 2006/0058252 A1    Mar. 16, 2006

Related U.S. Application Data

(60) Provisional application No. 60/449,066, filed on Feb. 21, 2003, provisional application No. 60/391,795, filed on Jun. 26, 2002, provisional application No. 60/417,997, filed on Oct. 14, 2002.

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl. ............. 514/44; 536/23.1; 536/23.72; 536/24.1; 536/24.5; 435/6

(58) Field of Classification Search .............. None
See application file for complete search history.

(56) References Cited

U.S. PATENT DOCUMENTS

| 4,511,713 | A | 4/1985 | Miller et al. |
|---|---|---|---|
| 4,560,678 | A | 12/1985 | Ranson |
| 4,689,320 | A | 8/1987 | Kaji |
| 4,740,463 | A | 4/1988 | Weinberg et al. |
| 4,814,268 | A | 3/1989 | Kreider et al. |
| 4,849,331 | A | 7/1989 | Lorincz |
| 4,849,332 | A | 7/1989 | Lorincz |
| 4,849,334 | A | 7/1989 | Lorincz |
| 4,908,306 | A | 3/1990 | Lorincz |
| 4,983,728 | A | 1/1991 | Herzog et al. |
| 5,023,243 | A | 6/1991 | Tullis |
| 5,053,024 | A * | 10/1991 | Dvoretzky ............ 604/291 |
| 5,057,411 | A | 10/1991 | Lancaster et al. |
| 5,071,757 | A | 12/1991 | Kreider et al. |
| 5,126,331 | A | 6/1992 | Gazzani |
| 5,142,032 | A | 8/1992 | Grimmel et al. |
| 5,187,090 | A | 2/1993 | de Villiers et al. |
| 5,190,931 | A | 3/1993 | Inouye |
| 5,272,065 | A | 12/1993 | Inouye et al. |
| 5,334,761 | A | 8/1994 | Gebeyehu et al. |
| 5,411,857 | A | 5/1995 | Beaudenon et al. |
| 5,457,189 | A | 10/1995 | Crooke et al. |
| 5,491,133 | A | 2/1996 | Walder et al. |
| 5,543,417 | A | 8/1996 | Waldstreicher |
| 5,554,538 | A | 9/1996 | Cole et al. |
| 5,578,475 | A | 11/1996 | Jessee |
| 5,580,547 | A | 12/1996 | Gilchrest et al. |
| 5,589,466 | A | 12/1996 | Felgner et al. |
| 5,591,574 | A | 1/1997 | Orth et al. |
| 5,595,884 | A | 1/1997 | Androphy et al. |
| 5,627,159 | A | 5/1997 | Shih et al. |
| 5,643,715 | A | 7/1997 | Lancaster |
| 5,656,423 | A | 8/1997 | Orth et al. |
| 5,665,580 | A | 9/1997 | Crooke et al. |
| 5,674,835 | A | 10/1997 | Androphy et al. |
| 5,681,944 | A | 10/1997 | Crooke et al. |
| 5,712,092 | A | 1/1998 | Orth et al. |
| 5,736,392 | A | 4/1998 | Hawley-Nelson et al. |
| 5,739,013 | A | 4/1998 | Budowsky et al. |
| 5,756,282 | A | 5/1998 | Crooke et al. |
| 5,776,502 | A | 7/1998 | Foulkes et al. |
| 5,811,232 | A | 9/1998 | Crooke et al. |
| 5,821,050 | A | 10/1998 | Cowsert et al. |

(Continued)

FOREIGN PATENT DOCUMENTS

| EP | 477 972 | 9/1996 |
|---|---|---|
| WO | WO 93/20095 | 10/1993 |
| WO | WO 95/28942 | 11/1995 |
| WO | WO 96/20013 | 7/1996 |
| WO | WO 97/27206 | 7/1997 |
| WO | WO 98/04575 | 2/1998 |
| WO | WO 98/37240 | 8/1998 |
| WO | WO 99/14377 | 3/1999 |
| WO | WO 00/09673 | 2/2000 |

(Continued)

OTHER PUBLICATIONS

U.S. Appl. No. 60/449,066, filed Feb. 21, 2003, Clawson.
GenBank Accession No. K02718 dated Mar. 18, 1994, 6 pages.
GenBank Accession No. M14119 dated Jun. 2, 1994, 6 pages.
GenBank Accession No. X05015 dated Apr. 18, 2005, 6 pages.

(Continued)

*Primary Examiner*—Sean R McGarry
(74) *Attorney, Agent, or Firm*—Fish & Richardson P.C.

(57) ABSTRACT

The invention provides methods and materials related to treating HPV infections (e.g., HPV infections of cutaneous and mucosal epithelial cells) and HPV-associated conditions (e.g., cervical dysplasia, HPV-associated cervical carcinomas, oral mucosal papilloma cancers, laryngeal papilloma cancers).

22 Claims, 10 Drawing Sheets

U.S. PATENT DOCUMENTS

| | | | |
|---|---|---|---|
| 5,824,519 | A | 10/1998 | Norris et al. |
| 5,837,856 | A | 11/1998 | Arnold, Jr. et al. |
| 5,876,922 | A | 3/1999 | Orth et al. |
| 5,919,619 | A | 7/1999 | Tullis |
| 5,952,487 | A | 9/1999 | Philipp et al. |
| 5,955,597 | A | 9/1999 | Arnold, Jr. et al. |
| 5,962,425 | A | 10/1999 | Walder et al. |
| 5,981,173 | A | 11/1999 | Orth et al. |
| 5,986,083 | A | 11/1999 | Dwyer et al. |
| 6,020,202 | A | 2/2000 | Jessee |
| 6,022,863 | A | 2/2000 | Peyman |
| 6,025,163 | A | 2/2000 | Shamanin et al. |
| 6,028,188 | A | 2/2000 | Arnold, Jr. et al. |
| 6,051,429 | A | 4/2000 | Hawley-Nelson et al. |
| 6,060,456 | A | 5/2000 | Arnold, Jr. et al. |
| 6,075,012 | A | 6/2000 | Gebeyehu et al. |
| 6,084,090 | A | 7/2000 | DiPaolo et al. |
| 6,087,341 | A | 7/2000 | Khavari et al. |
| 6,107,086 | A | 8/2000 | Cole et al. |
| 6,127,164 | A | 10/2000 | de Villiers et al. |
| 6,136,332 | A | 10/2000 | Grollier et al. |
| 6,172,048 | B1 | 1/2001 | Behr et al. |
| 6,174,870 | B1 * | 1/2001 | Crooke et al. ............... 514/44 |
| 6,271,359 | B1 | 8/2001 | Norris et al. |
| 6,326,174 | B1 | 12/2001 | Joyce et al. |
| 6,506,559 | B1 | 1/2003 | Fire et al. |
| 6,821,523 | B2 * | 11/2004 | Maibach et al. ............. 424/400 |
| 6,896,888 | B1 * | 5/2005 | Bohle et al. ............. 424/248.1 |
| 7,575,918 | B2 * | 8/2009 | Norris et al. ............. 435/320.1 |
| 2002/0114784 | A1 * | 8/2002 | Li et al. ..................... 424/93.2 |
| 2004/0209263 | A1 * | 10/2004 | Clawson et al. ................ 435/6 |
| 2004/0220123 | A1 * | 11/2004 | Norris et al. .................. 514/44 |
| 2004/0235171 | A1 * | 11/2004 | Milner ....................... 435/456 |
| 2004/0259247 | A1 * | 12/2004 | Tuschl et al. ................ 435/375 |
| 2006/0269530 | A1 * | 11/2006 | Clawson et al. .......... 424/93.21 |

FOREIGN PATENT DOCUMENTS

| | | |
|---|---|---|
| WO | WO 00/14244 | 3/2000 |
| WO | WO 00/34466 | 6/2000 |
| WO | WO 00/60115 | 10/2000 |
| WO | WO 02/46449 | 6/2002 |

OTHER PUBLICATIONS

Alvarez-Salas et al., "Inhibition of *HPV-16 E6/E7* immortalization of normal keratinocytes by hairpin ribozymes," *Proc. Natl. Acad. Sci. USA*, 1998, 95:1189-1194.

Alvarez-Salas et al., "Growth Inhibition of Cervical Tumor Cells by Antisense Oligodeoxynucleotides Directed to the Human Papillomavirus Type 16 E6 Gene," *Antisense Nucleic Acid Drug Dev.*, 1999, 9:441-450.

Benedict et al., "Triple ribozyme-mediated down-regulation of the retinoblastoma gene," *Carcinogenesis*, 1998, 19(7):1223-1230.

Beutner et al., "Treatment of genital warts with an immune-response modifier (iquimod)," *J. Am. Acad. Dermatol.*, 1998, 38:230-239.

Boletta et al., "High Efficient Non-Viral Gene Delivery to the Rat Kidney by Novel Polycationic Vectors," *J. Am. Soc. Nephrol.*, 1996, 7(9):1728, Abstract only.

Buhr et al., "Ribozyme termination of RNA transcripts down-regulate seed fatty acid genes in transgenic soybean," *Plant J.*, 2002, 30(2):155-163.

Chen et al., "Effectiveness of three ribozymes for cleavage of an RNA transcript from human papillomavirus type 18," *Cancer Gene Ther.*, 1995, 2(4):263-271.

Choo et al., "Retrovirus-Mediated Delivery of HPV16 E7 Antisense RNA Inhibited Tumorigenicity of CaSki Cells," *Gynecol. Oncol.*, 2000, 78:293-301.

Crone et al., "Growth Inhibition by a Triple Ribozyme Targeted to Repetitive B2 Transcripts," *Hepatology*, 1999, 29:1114-1123.

Feldman and Sen, "A New and Efficient DNA Enzyme for the Sequence-specific Cleavage of RNA," *J. Mol. Biol.*, 2001, 313:283-294.

Garber, "Prescription RNA," *Technology Review*, 2002, pp. 42-48.

Herasse et al., "Expression and Functional Characteristics of Calpain 3 Isoforms Generated through Tissue-Specific Transcriptional and Posttranscriptional Events," *Mol. Cell. Biol.*, 1999, 19(6):4047-4055.

Jiang and Milner, "Selective silencing of viral gene expression in HPV-positive human cervical carcinoma cells treated with siRNA, a primer of RNA interference," *Oncogene*, 2002, 21:6041-6048.

Kreider et al., "Laboratory Production In Vivo of Infectious Human Papillomavirus Type 11," *J. Virol.*, 1987, 61(2):590-593.

Kunke et al., "Preclinical study on gene therapy of cervical carcinoma using adeno-associated virus vectors," *Cancer Gene Ther.*, 2000, 7(5):766-777.

Laemmli, "Cleavage of Structural Proteins during the Assembly of the Head of Bacteriophage T4," *Nature*, 1970, 227:680-685.

Lewis et al., "Non-specific antiviral activity of antisense molecules targeted to the E1 region of human papillomavirus," *Antiviral Res.*, 2000, 48:187-196.

Lieber and Strauss, "Selection of Efficient Cleavage Sites in Target RNAs by Using a Ribozyme Expression Library," *Mol. Cell. Biol.*, 1995, 15(1):540-551.

Madrigal et al., "In Vitro Antigene Therapy Targeting HPV-16 E6 and E7 in Cervical Carcinoma," *Gynecol. Oncol.*, 1997, 64:18-25.

Nedbal and Sczakiel, "Hammerhead Ribozyme Activity in the Presence of Low Molecular Weight Cellular Extract," *Antisense Nucleic Acid Drug Dev.*, 1997, 7:585-589.

Okumoto et al., "Factors that Contribute to Efficient Catalytic Activity of a Small $Ca^{2+}$-Dependent Deoxyribozyme in Relation to Its RNA Cleavage Function," *Biochemistry*, 2003, 42(7):2158-2165.

Pan et al. "A selection system for identifying accessible sites in target RNAs," *RNA*, 2001, 7:610-621.

Pan et al., "Rapid identification of efficient target cleavage sites using a hammerhead ribozyme library in an iterative manner," *Mol. Therapy*, 2003, 7:129-139.

Pfaffl et al., "Relative expression software tool (REST ©) for group-wise comparison and statistical analysis of relative expression results in real-time PCR," *Nucl. Acids Res.*, 2002, 30(9):e36, 10 pages.

Rorke, "Antisense Human Papillomavirus (HPV) E6/E7 Expression, Reduced Stability of Epidermal Growth Factor, and Diminished Growth of HPV-Positive Tumor Cells," *J. Natl. Can. Inst.*, 1997, 89(17):1243-1246.

Santiago et al., "New DNA Enzyme Targeting Egr-1 mRNA Inhibits Vascular Smooth Muscle Proliferation and Regrowth after Injury," *Nat. Med.*, 1999, 5(11):1264-1269.

Santoro and Joyce, "A general purpose RNA-cleaving DNA enzyme," *Proc. Natl. Acad. Sci. USA*, 1997, 94(9):4262-4266.

Schwarze et al., "In Vivo Protein Transduction: Delivery of a Biologically Active Protein Into the Mouse," *Science*, 1999, 285:1569-1572.

Slebos et al., "p53-dependent $G_1$ arrest involves pRB-related proteins and is disrupted by the human papillomavirus 16 E7 oncoprotein," *Proc. Natl. Acad. Sci. USA*, 1994, 91:5320-5324.

Stacey et al., "Scanning the structure and antigenicity of HPV-16 E6 and E7 oncoproteins using antipeptide antibodies," *Oncogene*, 1994, 9:635-645.

Takagi et al., "Mechanism of action of hammerhead ribozymes and their applications in vivo: rapid identification of functional genes in the post-genome era by novel hybrid ribozyme libraries," *Biochem. Soc. Trans.*, 2002, 30(6):1145-1149.

Tan and Ting, "In Vitro and in Vivo Inhibition of Human Papillomavirus Type 16 *E6* and *E7* Genes," *Cancer Res.*, 1995, 55:4599-4605.

Templeton et al., "Improved DNA: liposome complexes for increased systemic delivery and gene expression," *Nat. Biotechnol.*, 1997, 15:647-652.

Venturini et al., "Kinetic selection of HPV 16 *E6/E7*-directed antisense nucleic acids: anti-proliferative effects on HPV 16-transformed cells," *Nucl. Acids Res.*, 1999. 27(7):1585-1592.

Walboomers et al., "Human Papillomavirus is a Necessary Cause of Invasive Cervical Cancer Worldwide," *J. Pathol.*, 1999, 189:12-19.

Walder et al., "Use of PCR primers containing a 3'-terminal ribose residue to prevent cross-contamination of amplified sequences," *Nucl. Acids Res.*, 1993, 21(18):4339-4343.

Zhang et al., "Involvement of the Fungal Nuclear Migration Gene *nudC* Human Homolog in Cell Proliferation and Mitotic Spindle Formation," *Exp. Cell Res.*, 2002, 273:73-84.

Zheng et al., "Effects of anti-HPV16E6-ribozyme on phenotype and gene expression of a cervical cancer cell line," *Chin. Med. J.*, 2002, 115(10):1501-1506.

zur Hausen, "Molecular Pathogenesis of Cancer of the Cervix and Its Causation by Specific Human Papillomavirus Types," *Curr. Top. Microbiol. Immunol.*, 1994, 186:131-156.

* cited by examiner

```
TS-17 Primer
5'-CAGGAAACAGCTATGAC-3'
5'-CAGGAAACAGCTATGACNNNNNNNNNRGGCTAGCTACAACGANNNNNNNNNCTGGCCGTCGTTTACA-3'
                                                    3'-GACCGGCAGCAAAATGT-5'
                                                           BS-17 Primer
```

↓ PCR

```
5'-CAGGAAACAGCTATGACNNNNNNNNNRGGCTAGCTACAACGANNNNNNNNNCTGGCCGTCGTTTACA-3'
3'-GTCCTTTGTCGATACTGNNNNNNNNNYCCGATCGATGTTGCTNNNNNNNNNGACCGGCAGCAAATGT-3'
```

B.

[gel image with lanes labeled TS-17, BS-17 (A C G T); and brackets labeling BS-17, 9N, Dz Core, R, 8N on bottom and TS-17, 8N, Y, -Dz Core, 9N on top]

C.

[schematic showing PCR/NaOH (TS$_D$ + BS$_R$), PCR/NaOH (TS$_D$), PCR/NaOH (TS$_R$), PCR/NaOH (TS$_R$ + BS$_D$) transformations with arrows]

A.
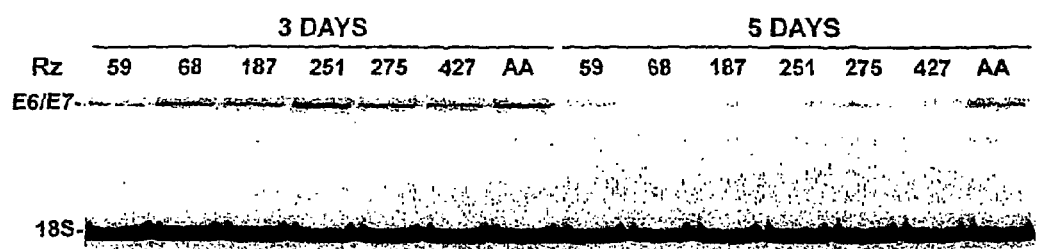
B.
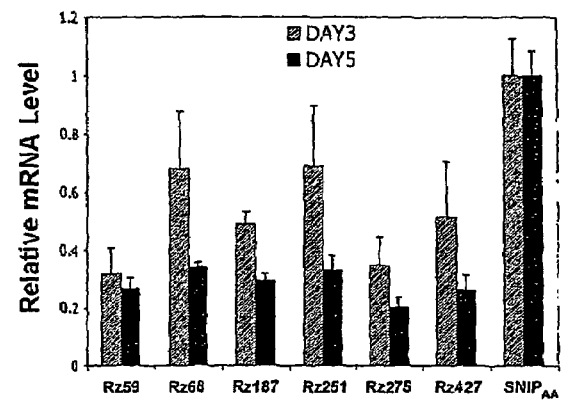
C.
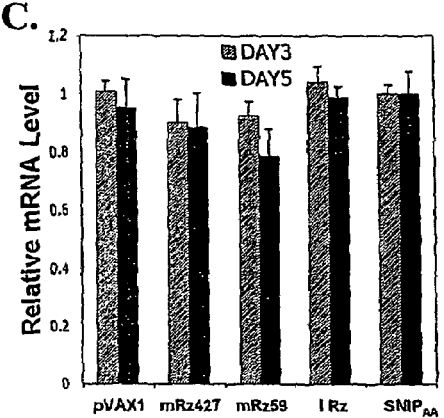
Figure 8

Figure 9
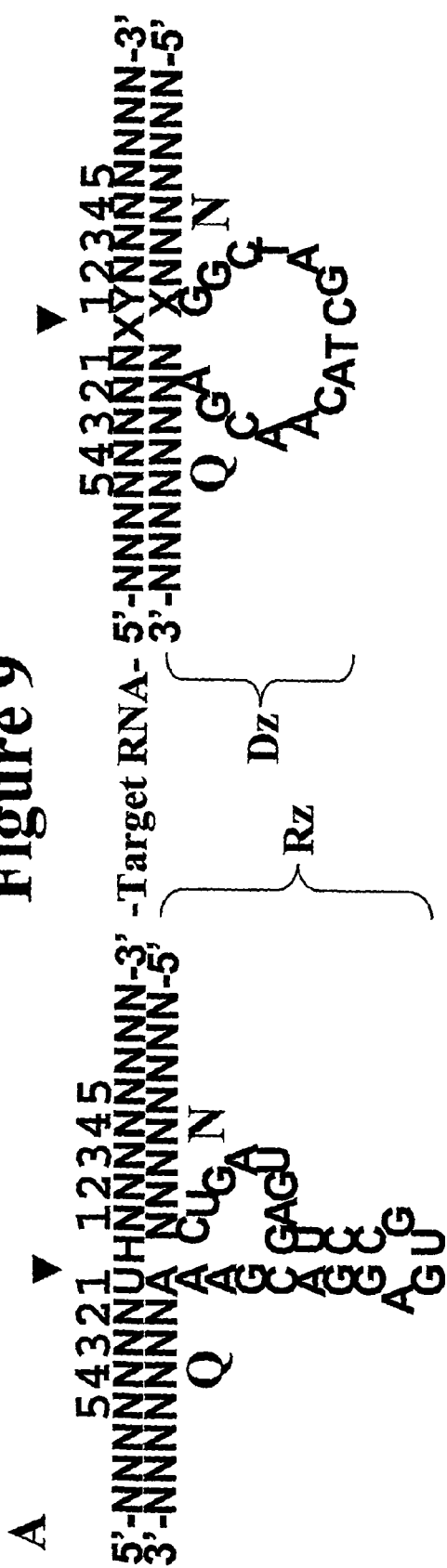
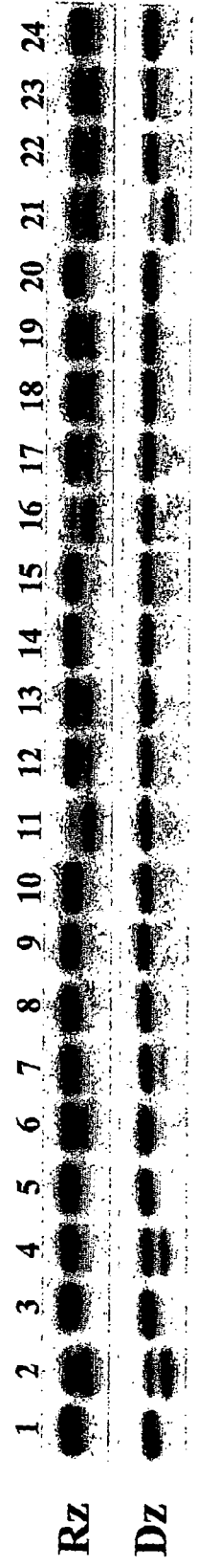

Figure 10
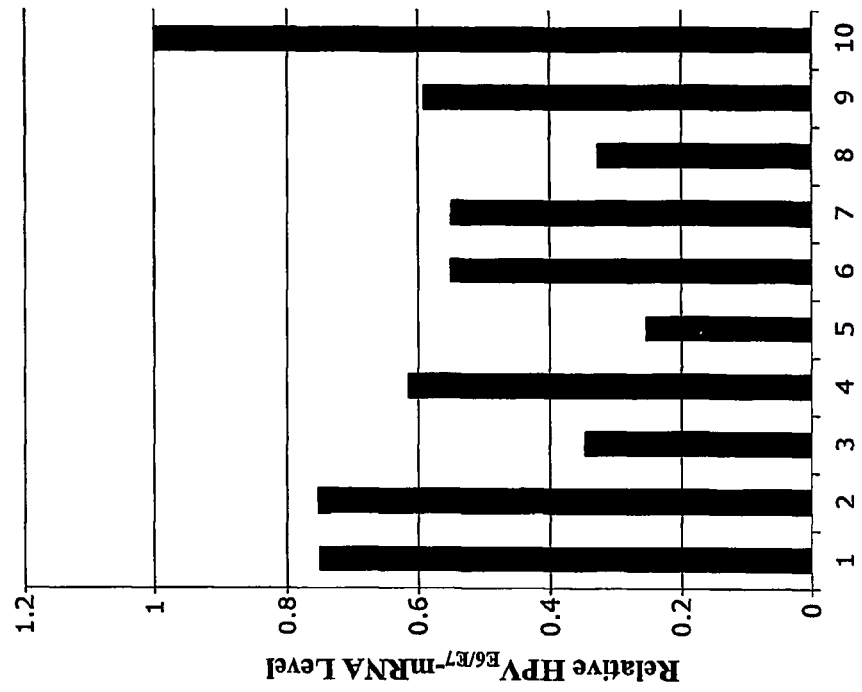
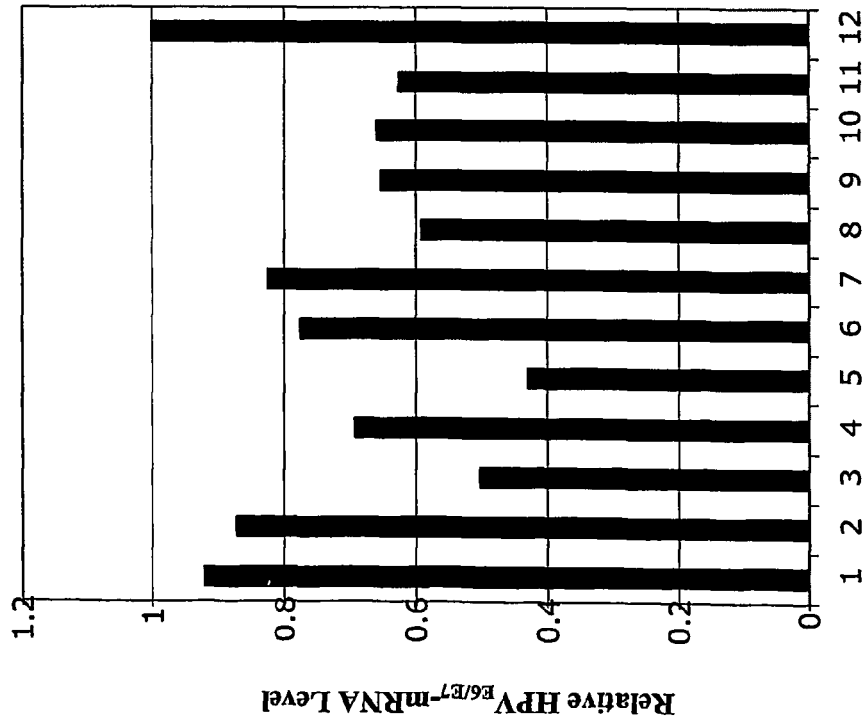

_US 7,704,965 B2_

SEQUENCE LISTING

<160> NUMBER OF SEQ ID NOS: 85

<210> SEQ ID NO 1
<211> LENGTH: 17
<212> TYPE: DNA
<213> ORGANISM: Artificial Sequence
<220> FEATURE:
<223> OTHER INFORMATION: primer

```
<400> SEQUENCE: 1
caggaaacag ctatgac                                                  17

<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
tgtaaaacga cggccag                                                  17

<210> SEQ ID NO 3
<211> LENGTH: 67
<212> TYPE: DNA
<213> ORGANISM: Artificial Sequence
<220> FEATURE:
<223> OTHER INFORMATION: exemplary catalytic nucleic acid
<221> NAME/KEY: misc_feature
<222> LOCATION: (1)...(67)
<223> OTHER INFORMATION: n = A,T,C or G

<400> SEQUENCE: 3
caggaaacag ctatgacnnn nnnnnrggct agctacaacg annnnnnnnn ctggccgtcg   60
ttttaca                                                             67

<210> SEQ ID NO 4
<211> LENGTH: 17
<212> TYPE: RNA
<213> ORGANISM: Artificial Sequence
<220> FEATURE:
<223> OTHER INFORMATION: HPV target sequence

<400> SEQUENCE: 4
ugcaauguuu caggacc                                                  17

<210> SEQ ID NO 5
<211> LENGTH: 17
<212> TYPE: RNA
<213> ORGANISM: Artificial Sequence
<220> FEATURE:
<223> OTHER INFORMATION: HPV target sequence

<400> SEQUENCE: 5
cccagaaagu uaccaca                                                  17

<210> SEQ ID NO 6
<211> LENGTH: 17
<212> TYPE: RNA
<213> ORGANISM: Artificial Sequence
<220> FEATURE:
<223> OTHER INFORMATION: HPV target sequence

<400> SEQUENCE: 6
uuaccacagu uaugcac                                                  17

<210> SEQ ID NO 7
<211> LENGTH: 17
<212> TYPE: RNA
<213> ORGANISM: Artificial Sequence
<220> FEATURE:
<223> OTHER INFORMATION: HPV target sequence
```

```
<400> SEQUENCE: 7
gacgugaggu auaugac                                              17

<210> SEQ ID NO 8
<211> LENGTH: 17
<212> TYPE: RNA
<213> ORGANISM: Artificial Sequence
<220> FEATURE:
<223> OTHER INFORMATION: HPV target sequence

<400> SEQUENCE: 8
cauaguauau agagaug                                              17

<210> SEQ ID NO 9
<211> LENGTH: 17
<212> TYPE: RNA
<213> ORGANISM: Artificial Sequence
<220> FEATURE:
<223> OTHER INFORMATION: HPV target sequence

<400> SEQUENCE: 9
auuagugagu auagaca                                              17

<210> SEQ ID NO 10
<211> LENGTH: 17
<212> TYPE: RNA
<213> ORGANISM: Artificial Sequence
<220> FEATURE:
<223> OTHER INFORMATION: HPV target sequence

<400> SEQUENCE: 10
uauaguuugu auggaac                                              17

<210> SEQ ID NO 11
<211> LENGTH: 17
<212> TYPE: RNA
<213> ORGANISM: Artificial Sequence
<220> FEATURE:
<223> OTHER INFORMATION: HPV target sequence

<400> SEQUENCE: 11
gccacugugu ccugaag                                              17

<210> SEQ ID NO 12
<211> LENGTH: 17
<212> TYPE: RNA
<213> ORGANISM: Artificial Sequence
<220> FEATURE:
<223> OTHER INFORMATION: HPV target sequence

<400> SEQUENCE: 12
uauaaggggu cggugga                                              17

<210> SEQ ID NO 13
<211> LENGTH: 17
<212> TYPE: RNA
<213> ORGANISM: Artificial Sequence
<220> FEATURE:
<223> OTHER INFORMATION: HPV target sequence

<400> SEQUENCE: 13
guggaccggu cgaugua                                              17
```

```
<210> SEQ ID NO 14
<211> LENGTH: 17
<212> TYPE: RNA
<213> ORGANISM: Artificial Sequence
<220> FEATURE:
<223> OTHER INFORMATION: HPV target sequence

<400> SEQUENCE: 14
aaagaugccu ccacguc                                                  17

<210> SEQ ID NO 15
<211> LENGTH: 17
<212> TYPE: RNA
<213> ORGANISM: Artificial Sequence
<220> FEATURE:
<223> OTHER INFORMATION: HPV target sequence

<400> SEQUENCE: 15
accuaaaggu ugugugg                                                  17

<210> SEQ ID NO 16
<211> LENGTH: 17
<212> TYPE: RNA
<213> ORGANISM: Artificial Sequence
<220> FEATURE:
<223> OTHER INFORMATION: HPV target sequence

<400> SEQUENCE: 16
uagacacuuu aauuaug                                                  17

<210> SEQ ID NO 17
<211> LENGTH: 17
<212> TYPE: RNA
<213> ORGANISM: Artificial Sequence
<220> FEATURE:
<223> OTHER INFORMATION: HPV target sequence

<400> SEQUENCE: 17
ugugugaaau agaaaaa                                                  17

<210> SEQ ID NO 18
<211> LENGTH: 17
<212> TYPE: RNA
<213> ORGANISM: Artificial Sequence
<220> FEATURE:
<223> OTHER INFORMATION: HPV target sequence

<400> SEQUENCE: 18
guggaagggu cguugcu                                                  17

<210> SEQ ID NO 19
<211> LENGTH: 17
<212> TYPE: RNA
<213> ORGANISM: Artificial Sequence
<220> FEATURE:
<223> OTHER INFORMATION: HPV target sequence

<400> SEQUENCE: 19
gaagacuugu uacccua                                                  17

<210> SEQ ID NO 20
<211> LENGTH: 17
<212> TYPE: RNA
<213> ORGANISM: Artificial Sequence
<220> FEATURE:
<223> OTHER INFORMATION: HPV target sequence
```

```
<400> SEQUENCE: 20
ccuguagggu uacauug                                                 17

<210> SEQ ID NO 21
<211> LENGTH: 17
<212> TYPE: RNA
<213> ORGANISM: Artificial Sequence
<220> FEATURE:
<223> OTHER INFORMATION: HPV target sequence

<400> SEQUENCE: 21
gaagacagcu cagaaga                                                 17

<210> SEQ ID NO 22
<211> LENGTH: 17
<212> TYPE: RNA
<213> ORGANISM: Artificial Sequence
<220> FEATURE:
<223> OTHER INFORMATION: HPV target sequence

<400> SEQUENCE: 22
auuaccaaau acugacc                                                 17

<210> SEQ ID NO 23
<211> LENGTH: 17
<212> TYPE: RNA
<213> ORGANISM: Artificial Sequence
<220> FEATURE:
<223> OTHER INFORMATION: HPV target sequence

<400> SEQUENCE: 23
cuuugaggau ccaacac                                                 17

<210> SEQ ID NO 24
<211> LENGTH: 17
<212> TYPE: RNA
<213> ORGANISM: Artificial Sequence
<220> FEATURE:
<223> OTHER INFORMATION: HPV target sequence

<400> SEQUENCE: 24
accguugaau ccagcag                                                 17

<210> SEQ ID NO 25
<211> LENGTH: 17
<212> TYPE: RNA
<213> ORGANISM: Artificial Sequence
<220> FEATURE:
<223> OTHER INFORMATION: HPV target sequence

<400> SEQUENCE: 25
ugggcacuau agaggcc                                                 17

<210> SEQ ID NO 26
<211> LENGTH: 17
<212> TYPE: DNA
<213> ORGANISM: Artificial Sequence
<220> FEATURE:
<223> OTHER INFORMATION: HPV target sequence

<400> SEQUENCE: 26
cccagaaagt taccaca                                                 17
```

```
<210> SEQ ID NO 27
<211> LENGTH: 17
<212> TYPE: DNA
<213> ORGANISM: Artificial Sequence
<220> FEATURE:
<223> OTHER INFORMATION: HPV target sequence

<400> SEQUENCE: 27
ttaccacagt tatgcac                                                  17

<210> SEQ ID NO 28
<211> LENGTH: 17
<212> TYPE: DNA
<213> ORGANISM: Artificial Sequence
<220> FEATURE:
<223> OTHER INFORMATION: HPV target sequence

<400> SEQUENCE: 28
gacgtgaggt atatgac                                                  17

<210> SEQ ID NO 29
<211> LENGTH: 17
<212> TYPE: DNA
<213> ORGANISM: Artificial Sequence
<220> FEATURE:
<223> OTHER INFORMATION: HPV target sequence

<400> SEQUENCE: 29
catagtatat agagatg                                                  17

<210> SEQ ID NO 30
<211> LENGTH: 17
<212> TYPE: DNA
<213> ORGANISM: Artificial Sequence
<220> FEATURE:
<223> OTHER INFORMATION: HPV target sequence

<400> SEQUENCE: 30
attagtgagt atagaca                                                  17

<210> SEQ ID NO 31
<211> LENGTH: 17
<212> TYPE: DNA
<213> ORGANISM: Artificial Sequence
<220> FEATURE:
<223> OTHER INFORMATION: HPV target sequence

<400> SEQUENCE: 31
tatagtttgt atggaac                                                  17

<210> SEQ ID NO 32
<211> LENGTH: 17
<212> TYPE: DNA
<213> ORGANISM: Artificial Sequence
<220> FEATURE:
<223> OTHER INFORMATION: HPV target sequence

<400> SEQUENCE: 32
tataaggggt cggtgga                                                  17

<210> SEQ ID NO 33
<211> LENGTH: 17
<212> TYPE: DNA
<213> ORGANISM: Artificial Sequence
<220> FEATURE:
<223> OTHER INFORMATION: HPV target sequence
```

```
<400> SEQUENCE: 33
gtggaccggt cgatgta                                                    17

<210> SEQ ID NO 34
<211> LENGTH: 17
<212> TYPE: DNA
<213> ORGANISM: Artificial Sequence
<220> FEATURE:
<223> OTHER INFORMATION: HPV target sequence

<400> SEQUENCE: 34
ggaggaggat gaaatag                                                    17

<210> SEQ ID NO 35
<211> LENGTH: 17
<212> TYPE: DNA
<213> ORGANISM: Artificial Sequence
<220> FEATURE:
<223> OTHER INFORMATION: HPV target sequence

<400> SEQUENCE: 35
gcctccacgt ctgcaac                                                    17

<210> SEQ ID NO 36
<211> LENGTH: 17
<212> TYPE: DNA
<213> ORGANISM: Artificial Sequence
<220> FEATURE:
<223> OTHER INFORMATION: HPV target sequence

<400> SEQUENCE: 36
acctaaaggt tgtgtgg                                                    17

<210> SEQ ID NO 37
<211> LENGTH: 17
<212> TYPE: DNA
<213> ORGANISM: Artificial Sequence
<220> FEATURE:
<223> OTHER INFORMATION: HPV target sequence

<400> SEQUENCE: 37
attaaccaat atagaca                                                    17

<210> SEQ ID NO 38
<211> LENGTH: 17
<212> TYPE: DNA
<213> ORGANISM: Artificial Sequence
<220> FEATURE:
<223> OTHER INFORMATION: HPV target sequence

<400> SEQUENCE: 38
ttacctgtgt cacaagc                                                    17

<210> SEQ ID NO 39
<211> LENGTH: 17
<212> TYPE: DNA
<213> ORGANISM: Artificial Sequence
<220> FEATURE:
<223> OTHER INFORMATION: HPV target sequence

<400> SEQUENCE: 39
gccgttgtgt gaaatag                                                    17
```

```
<210> SEQ ID NO 40
<211> LENGTH: 17
<212> TYPE: DNA
<213> ORGANISM: Artificial Sequence
<220> FEATURE:
<223> OTHER INFORMATION: HPV target sequence

<400> SEQUENCE: 40
gtggaagggt cgttgct                                                    17

<210> SEQ ID NO 41
<211> LENGTH: 17
<212> TYPE: DNA
<213> ORGANISM: Artificial Sequence
<220> FEATURE:
<223> OTHER INFORMATION: HPV target sequence

<400> SEQUENCE: 41
gaagacttgt taccta                                                     17

<210> SEQ ID NO 42
<211> LENGTH: 17
<212> TYPE: DNA
<213> ORGANISM: Artificial Sequence
<220> FEATURE:
<223> OTHER INFORMATION: HPV target sequence

<400> SEQUENCE: 42
agaagacagc tcagaag                                                    17

<210> SEQ ID NO 43
<211> LENGTH: 17
<212> TYPE: DNA
<213> ORGANISM: Artificial Sequence
<220> FEATURE:
<223> OTHER INFORMATION: HPV target sequence

<400> SEQUENCE: 43
attaccaaat actgacc                                                    17

<210> SEQ ID NO 44
<211> LENGTH: 17
<212> TYPE: DNA
<213> ORGANISM: Artificial Sequence
<220> FEATURE:
<223> OTHER INFORMATION: HPV target sequence

<400> SEQUENCE: 44
ctttgaggat ccaacac                                                    17

<210> SEQ ID NO 45
<211> LENGTH: 17
<212> TYPE: DNA
<213> ORGANISM: Artificial Sequence
<220> FEATURE:
<223> OTHER INFORMATION: HPV target sequence

<400> SEQUENCE: 45
accgttgaat ccagcag                                                    17

<210> SEQ ID NO 46
<211> LENGTH: 17
<212> TYPE: DNA
<213> ORGANISM: Artificial Sequence
<220> FEATURE:
<223> OTHER INFORMATION: HPV target sequence
```

<400> SEQUENCE: 46
tgggcactat agaggcc    17

<210> SEQ ID NO 47
<211> LENGTH: 17
<212> TYPE: DNA
<213> ORGANISM: Artificial Sequence
<220> FEATURE:
<223> OTHER INFORMATION: HPV target sequence

<400> SEQUENCE: 47
gtgcttttgt gtgtctg    17

<210> SEQ ID NO 48
<211> LENGTH: 17
<212> TYPE: DNA
<213> ORGANISM: Artificial Sequence
<220> FEATURE:
<223> OTHER INFORMATION: HPV target sequence

<400> SEQUENCE: 48
gcctctgcgt ttaggtg    17

<210> SEQ ID NO 49
<211> LENGTH: 17
<212> TYPE: DNA
<213> ORGANISM: Artificial Sequence
<220> FEATURE:
<223> OTHER INFORMATION: oligonucleotide

<400> SEQUENCE: 49
agcaacgacc cttccac    17

<210> SEQ ID NO 50
<211> LENGTH: 18
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: 18
<223> OTHER INFORMATION: thymine is inverted

<400> SEQUENCE: 50
agcaacgacc cttccact    18

<210> SEQ ID NO 51
<211> LENGTH: 23
<212> TYPE: RNA
<213> ORGANISM: Artificial Sequence
<220> FEATURE:
<223> OTHER INFORMATION: catalytic nucleic acid core sequence

<400> SEQUENCE: 51
cugaugaguc cgugaggacg aaa    23

<210> SEQ ID NO 52
<211> LENGTH: 38
<212> TYPE: RNA
<213> ORGANISM: Artificial Sequence
<220> FEATURE:
<223> OTHER INFORMATION: exemplary catalytic nucleic acid sequence

<400> SEQUENCE: 52
uguggucuga ugaguccgug aggacgaaac uuucuggg    38

<210> SEQ ID NO 53
<211> LENGTH: 17
<212> TYPE: RNA
<213> ORGANISM: Artificial Sequence
<220> FEATURE:
<223> OTHER INFORMATION: 5' end flanking sequence of catalytic nucleic acid

<400> SEQUENCE: 53
agcucgaccu cagaucu                                                    17

<210> SEQ ID NO 54
<211> LENGTH: 39
<212> TYPE: RNA
<213> ORGANISM: Artificial Sequence
<220> FEATURE:
<223> OTHER INFORMATION: 3' end flanking sequence of catalytic nucleic acid

<400> SEQUENCE: 54
caauugaaaa aaaaaaaaaa aaaaaaaaaa aaaaaaguc                            39

<210> SEQ ID NO 55
<211> LENGTH: 13
<212> TYPE: RNA
<213> ORGANISM: Artificial Sequence
<220> FEATURE:
<223> OTHER INFORMATION: 5' end flanking sequence of catalytic nucleic acid

<400> SEQUENCE: 55
gguuccagga ucc                                                        13

<210> SEQ ID NO 56
<211> LENGTH: 39
<212> TYPE: RNA
<213> ORGANISM: Artificial Sequence
<220> FEATURE:
<223> OTHER INFORMATION: 3' end flanking sequence of catalytic nucleic acid

<400> SEQUENCE: 56
gaauucaaaa aaaaaaaaaa aaaaaaaaaa aaaaaaguc                            39

<210> SEQ ID NO 57
<211> LENGTH: 38
<212> TYPE: RNA
<213> ORGANISM: Artificial Sequence
<220> FEATURE:
<223> OTHER INFORMATION: HPV target sequence

<400> SEQUENCE: 57
ccacaccuga ugaguccgug aggacgaaac cuuuaggu                             38

<210> SEQ ID NO 58
<211> LENGTH: 38
<212> TYPE: RNA
<213> ORGANISM: Artificial Sequence
<220> FEATURE:
<223> OTHER INFORMATION: HPV target sequence

<400> SEQUENCE: 58
cauaaucuga ugaguccgug aggacgaaaa agugcua                              38

<210> SEQ ID NO 59
<211> LENGTH: 38
<212> TYPE: RNA
<213> ORGANISM: Artificial Sequence
<220> FEATURE:
<223> OTHER INFORMATION: HPV target sequence

<400> SEQUENCE: 59
agcaaccuga ugaguccgug aggacgaaac ccuuccac                                  38

<210> SEQ ID NO 60
<211> LENGTH: 76
<212> TYPE: DNA
<213> ORGANISM: Artificial Sequence
<220> FEATURE:
<223> OTHER INFORMATION: HPV target sequence (combined DNA and RNA)

<400> SEQUENCE: 60
agcaaccuga ugaguccgug aggacgaaac ccuuccaccc acaccugaug aguccgugag          60
gacgaaaaag tgtcta                                                          76

<210> SEQ ID NO 61
<211> LENGTH: 76
<212> TYPE: RNA
<213> ORGANISM: Artificial Sequence
<220> FEATURE:
<223> OTHER INFORMATION: HPV target sequence

<400> SEQUENCE: 61
agcaaccuga ugaguccgug aggacgaaac ccuuccacca uaaucugaug aguccgugag          60
gacgaaaaag ugucua                                                          76

<210> SEQ ID NO 62
<211> LENGTH: 76
<212> TYPE: RNA
<213> ORGANISM: Artificial Sequence
<220> FEATURE:
<223> OTHER INFORMATION: HPV target sequence

<400> SEQUENCE: 62
agcaaccuga ugaguccgug aggacgaaac ccuuccacag caaccugaug aguccgugag          60
gacgaaaccc uuccac                                                          76

<210> SEQ ID NO 63
<211> LENGTH: 94
<212> TYPE: RNA
<213> ORGANISM: Artificial Sequence
<220> FEATURE:
<223> OTHER INFORMATION: HPV target sequence

<400> SEQUENCE: 63
agcucgaccu cagaucuagc aaccugauga guccgugagg acgaaacccu uccaccaauu          60
gaaaaaaaaa aaaaaaaaaa aaaaaaaaaa aguc                                      94

<210> SEQ ID NO 64
<211> LENGTH: 132
<212> TYPE: RNA
<213> ORGANISM: Artificial Sequence
<220> FEATURE:
<223> OTHER INFORMATION: HPV target sequence -continued

```
<400> SEQUENCE: 64
agcucgaccu cagaucuagc aaccugauga guccgugagg acgaaacccu uccacagcaa     60
ccugaugagu ccgugaggac gaaacccuuc caccaauuga aaaaaaaaa aaaaaaaaaa    120 aaaaaaaag uc                                                         132

<210> SEQ ID NO 65
<211> LENGTH: 31
<212> TYPE: DNA
<213> ORGANISM: Artificial Sequence
<220> FEATURE:
<223> OTHER INFORMATION: HPV target sequence

<400> SEQUENCE: 65
gttgcagagg ctagctacaa cgagtggagg c                                    31

<210> SEQ ID NO 66
<211> LENGTH: 31
<212> TYPE: DNA
<213> ORGANISM: Artificial Sequence
<220> FEATURE:
<223> OTHER INFORMATION: HPV target sequence

<400> SEQUENCE: 66
ctatttcagg ctagctacaa cgaacaacgg c                                    31

<210> SEQ ID NO 67
<211> LENGTH: 31
<212> TYPE: DNA
<213> ORGANISM: Artificial Sequence
<220> FEATURE:
<223> OTHER INFORMATION: HPV target sequence

<400> SEQUENCE: 67
agcaacgagg ctagctacaa cgaccttcca c                                    31

<210> SEQ ID NO 68
<211> LENGTH: 15
<212> TYPE: DNA
<213> ORGANISM: Artificial Sequence
<220> FEATURE:
<223> OTHER INFORMATION: catalytic nucleic acid core sequence

<400> SEQUENCE: 68
ggctagctac aacga                                                      15

<210> SEQ ID NO 69
<211> LENGTH: 31
<212> TYPE: DNA
<213> ORGANISM: Artificial Sequence
<220> FEATURE:
<223> OTHER INFORMATION: HPV target sequence

<400> SEQUENCE: 69
agcaacgagc ctagctacta cgaccttcca c                                    31

<210> SEQ ID NO 70
<211> LENGTH: 31
<212> TYPE: DNA
<213> ORGANISM: Artificial Sequence
<220> FEATURE:
<223> OTHER INFORMATION: HPV target sequence

<400> SEQUENCE: 70
tccgaagagg ctagctacaa cgagacaaga t                                    31
```

<210> SEQ ID NO 71
<211> LENGTH: 31
<212> TYPE: DNA
<213> ORGANISM: Artificial Sequence
<220> FEATURE:
<223> OTHER INFORMATION: HPV target sequence

<400> SEQUENCE: 71
tccgaagagc ctagctacta cgagacaaga t                                 31

<210> SEQ ID NO 72
<211> LENGTH: 25
<212> TYPE: DNA
<213> ORGANISM: Artificial Sequence
<220> FEATURE:
<223> OTHER INFORMATION: probe

<400> SEQUENCE: 72
ctttcccttt gcagcgtgtg cctgt                                        25

<210> SEQ ID NO 73
<211> LENGTH: 24
<212> TYPE: DNA
<213> ORGANISM: Artificial Sequence
<220> FEATURE:
<223> OTHER INFORMATION: primer

<400> SEQUENCE: 73
ctggaaaacc caacttctgt acaa                                         24

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
accacggcac tgattttcag t                                            21

<210> SEQ ID NO 75
<211> LENGTH: 25
<212> TYPE: DNA
<213> ORGANISM: Artificial Sequence
<220> FEATURE:
<223> OTHER INFORMATION: probe

<400> SEQUENCE: 75
tgtgcacagg agccaagagt gaaga                                        25

<210> SEQ ID NO 76
<211> LENGTH: 17
<212> TYPE: PRT
<213> ORGANISM: Artificial Sequence
<220> FEATURE:
<223> OTHER INFORMATION: synthetically generated polypeptide

<400> SEQUENCE: 76

His Gly Arg Leu Val Thr Leu Lys Asp Ile Val Leu Asp Leu Gln Pro
1               5                   10                  15

Cys

<210> SEQ ID NO 77
<211> LENGTH: 17
<212> TYPE: PRT
<213> ORGANISM: Artificial Sequence

```
<220> FEATURE:
<223> OTHER INFORMATION: synthetically generated polypeptide

<400> SEQUENCE: 77

Met Glu Ser Lys Asp Ala Ser Thr Ser Ala Thr Ser Ile Asp Gln Leu
1               5                   10                  15

Cys

<210> SEQ ID NO 78
<211> LENGTH: 17
<212> TYPE: PRT
<213> ORGANISM: Artificial Sequence
<220> FEATURE:
<223> OTHER INFORMATION: synthetically generated polypeptide

<400> SEQUENCE: 78

Leu Glu Leu Gln Gly Lys Ile Asn Gln Tyr Arg His Phe Asn Tyr Ala
1               5                   10                  15

Cys

<210> SEQ ID NO 79
<211> LENGTH: 17
<212> TYPE: DNA
<213> ORGANISM: Artificial Sequence
<220> FEATURE:
<223> OTHER INFORMATION: exemplary catalytic nucleic acid sequence

<400> SEQUENCE: 79
tgtaaaacga cggccag                                                17

<210> SEQ ID NO 80
<211> LENGTH: 67
<212> TYPE: DNA
<213> ORGANISM: Artificial Sequence
<220> FEATURE:
<223> OTHER INFORMATION: exemplary catalytic nucleic acid (complementary
      strand)
<221> NAME/KEY: misc_feature
<222> LOCATION: (1)...(67)
<223> OTHER INFORMATION: n = A,T,C or G

<400> SEQUENCE: 80
tgtaaaacga cggccagnnn nnnnnntcgt tgtagctagc cynnnnnnnn gtcatagctg    60
tttcctg                                                             67

<210> SEQ ID NO 81
<211> LENGTH: 17
<212> TYPE: DNA
<213> ORGANISM: Artificial Sequence
<220> FEATURE:
<223> OTHER INFORMATION: exemplary 5? end flanking sequence of catalytic
      nucleic acid

<400> SEQUENCE: 81
aaaaaaaaaa aaaaaaa                                                17

<210> SEQ ID NO 82
<211> LENGTH: 17
<212> TYPE: DNA
<213> ORGANISM: Artificial Sequence
<220> FEATURE:
<223> OTHER INFORMATION: exemplary 3? end flanking sequence of catalytic
      nucleic acid
```

<400> SEQUENCE: 82
tgtaaaacga cggccag                                                        17

<210> SEQ ID NO 83
<211> LENGTH: 38
<212> TYPE: RNA
<213> ORGANISM: Artificial Sequence
<220> FEATURE:
<223> OTHER INFORMATION: exemplary catalytic nucleic acid
<221> NAME/KEY: misc_feature
<222> LOCATION: (1)...(38)
<223> OTHER INFORMATION: n = A, U,C or G

<400> SEQUENCE: 83
nnnnnnnncu gaugaguccg ugaggacgaa annnnnnn                                 38

<210> SEQ ID NO 84
<211> LENGTH: 31
<212> TYPE: DNA
<213> ORGANISM: Artificial Sequence
<220> FEATURE:
<223> OTHER INFORMATION: exemplary catalytic nucleic acid
<221> NAME/KEY: misc_feature
<222> LOCATION: (1)...(31)
<223> OTHER INFORMATION: n = A,T,C or G

<400> SEQUENCE: 84
nnnnnnnngg ctagctacaa cgannnnnnn n                                        31

<210> SEQ ID NO 85
<211> LENGTH: 7904
<212> TYPE: DNA
<213> ORGANISM: Human papilloma virus 16

<400> SEQUENCE: 85

| | | |
|---|---|---|
| actacaataa ttcatgtata aaactaaggg cgtaaccgaa atcggttgaa ccgaaaccgg | 60 |
| ttagtataaa agcagacatt ttatgcacca aaagagaact gcaatgtttc aggacccaca | 120 |
| ggagcgaccc agaaagttac cacagttatg cacagagctg caaacaacta tacatgatat | 180 |
| aatattagaa tgtgtgtact gcaagcaaca gttactgcga cgtgaggtat atgactttgc | 240 |
| ttttcgggat ttatgcatag tatatagaga tgggaatcca tatgctgtat gtgataaatg | 300 |
| tttaaagttt tattctaaaa ttagtgagta tagacattat tgttatagtt tgtatggaac | 360 |
| aacattagaa cagcaataca caaaccgtt gtgtgatttg ttaattaggt gtattaactg | 420 |
| tcaaaagcca ctgtgtcctg aagaaaagca agacatctg acaaaaagc aaagattcca | 480 |
| taatataagg ggtcggtgga ccggtcgatg tatgtcttgt tgcagatcat caagaacacg | 540 |
| tagagaaacc cagctgtaat catgcatgga gatacaccta cattgcatga atatatgtta | 600 |
| gatttgcaac cagagacaac tgatctctac tgttatgagc aattaaatga cagctcagag | 660 |
| gaggaggatg aaatagatgg tccagctgga caagcagaac cggacagagc ccattacaat | 720 |
| attgtaacct tttgttgcaa gtgtgactct acgcttcggt tgtgcgtaca aagcacacac | 780 |
| gtagacattc gtactttgga agacctgtta atgggcacac taggaattgt gtgccccatc | 840 |
| tgttctcaga aaccataatc taccatggct gatcctgcag gtaccaatgg ggaagagggt | 900 |
| acgggatgta atggatggtt ttatgtagag gctgtagtgg aaaaaaaac agggatgct | 960 |
| atatcgatg acgagaacga aaatgacagt gatacaggtg aagatttggt agatttata | 1020 |
| gtaaatgata atgattattt aacacaggca gaaacagaga cagcacatgc gttgtttact | 1080 |
| gcacaggaag caaaacaaca tagagatgca gtacaggttc taaaacgaaa gtatttggta | 1140 |

```
gtccacttag tgatattagt ggatgtgtag acaataatat tagtcctaga ttaaaagcta   1200
tatgtataga aaacaaagt agagctgcaa aaaggagatt atttgaaagc gaagacagcg     1260
ggtatggcaa tactgaagtg gaaactcagc agatgttaca ggtagaaggg cgccatgaga   1320
ctgaaacacc atgtagtcag tatagtggtg gaagtggggg tggttgcagt cagtacagta   1380
gtggaagtgg gggagagggt gttagtgaaa gacacactat atgccaaaca ccacttacaa   1440
atattttaaa tgtactaaaa actagtaatg caaaggcagc aatgttagca aaatttaaag   1500
agttatacgg ggtgagtttt tcagaattag taagaccatt taaaagtaat aaatcaacgt   1560
gttgcgattg gtgtattgct gcatttggac ttacacccag tatagctgac agtataaaaa   1620
cactattaca acaatattgt ttatatttac acattcaaag tttagcatgt tcatggggaa   1680
tggttgtgtt actattagta agatataaat gtggaaaaaa tagagaaaca attgaaaaat   1740
tgctgtctaa actattatgt gtgtctccaa tgtgtatgat gatagagcct ccaaaattgc   1800
gtagtacagc agcagcatta tattggtata aacaggtat atcaaatatt agtgaagtgt   1860
atggagacac gccagaatgg atacaaagac aaacagtatt acaacatagt tttaatgatt   1920
gtacatttga attatcacag atggtacaat gggcctacga taatgacata gtagacgata   1980
gtgaaattgc atataaatat gcacaattgg cagacactaa tagtaatgca agtgcctttc   2040
taaaaagtaa ttcacaggca aaaattgtaa aggattgtgc aacaatgtgt agacattata   2100
aacgagcaga aaaaaaacaa atgagtatga gtcaatggat aaaatataga tgtgataggg   2160
tagatgatgg aggtgattgg aagcaaattg ttatgttttt aaggtatcaa ggtgtagagt   2220
ttatgtcatt tttaactgca ttaaaaagat ttttgcaagg catacctaaa aaaaattgca   2280
tattactata tggtgcagct aacacaggta aatcattatt tggtatgagt ttaatgaaat   2340
ttctgcaagg gtctgtaata tgttttgtaa attctaaaag ccattttggg ttacaaccat   2400
tagcagatgc caaaataggt atgttagatg atgctacagt gccctgttgg aactacatag   2460
atgacaattt aagaaatgca ttggatggaa atttagtttc tatggatgta aagcatagac   2520
cattggtaca actaaaatgc cctccattat taattcatc taacattaat gctggtacag   2580
attctaggtg gccttattta cataatagat tggtggtgtt tacatttcct aatgagtttc   2640
catttgacga aaacgaaat ccagtgtatg agcttaatga taagaactgg aaatcctttt     2700
tctcaaggac gtggtccaga ttaagtttgc acgaggacga ggacaaggaa aacgatggag   2760
actctttgcc aacgtttaaa tgtgtgtcag gacaaaatac taacacatta tgaaaatgat    2820
agtacagacc tacgtgacca tatagactat tggaaacaca tgcgcctaga atgtgctatt   2880
tattacaagg ccagagaaat gggatttaaa catattaacc accaagtggt gccaacactg   2940
gctgtatcaa agaataaagc attacaagca attgaactgc aactaacgtt agaaacaata   3000
tataactcac aatatagtaa tgaaaagtgg acattacaag acgttagcct tgaagtgtat   3060
ttaactgcac caacaggatg tataaaaaaa catggatata cagtggaagt gcagtttgat   3120
ggagacatat gcaatacaat gcattataca aactggacac atatatatat ttgtgaagaa   3180
gcatcagtaa ctgtggtaga gggtcaagtt gactattatg gtttatatta tgttcatgaa   3240
ggaatacgaa catattttgt gcagtttaaa gatgatgcag aaaaatatag taaaaataaa   3300
gtatgggaag ttcatgcggg tggtcaggta atattatgtc ctacatctgt gtttagcagc   3360
aacgaagtat cctctcctga aattattagg cagcacttgg ccaaccaccc cgccgcgacc   3420
cataccaaag ccgtcgcctt gggcaccgaa gaaacacaga cgactatcca gcgaccaaga   3480
tcagagccag acaccggaaa cccctgccac accactaagt tgttgcacag agactcagtg   3540
```

```
gacagtgctc caatcctcac tgcatttaac agctcacaca aaggacggat taactgtaat    3600
agtaacacta cacccatagt acatttaaaa ggtgatgcta atactttaaa atgtttaaga    3660
tatagattta aaaagcattg tacattgtat actgcagtgt cgtctacatg gcattggaca    3720
ggacataatg taaaacataa aagtgcaatt gttacactta catatgatag tgaatggcaa    3780
cgtgaccaat ttttgtctca agttaaaata ccaaaaacta ttacagtgtc tactggattt    3840
atgtctatat gacaaatctt gatactgcat ccacaacatt actggcgtgc ttttttgcttt   3900 gctttgtgtg cttttgtgtg tctgcctatt aatacgtccg ctgcttttgt ctgtgtctac    3960
atacacatca ttaataatat tggtattact attgtggata acagcagcct ctgcgtttag    4020
gtgttttatt gtatatatta tatttgttta taccattta ttttttaatac atacacatgc     4080 acgcttttta attacataat gtatatgtac ataatgtaat tgttacatat aattgttgta    4140
taccataact tactattttt tcttttttat tttcatatat aatttttttt tttgtttgtt    4200
tgtttgtttt ttaataaact gttattactt aacaatgcga cacaaacgtt ctgcaaaacg    4260
cacaaaacgt gcatcggcta cccaacttta taaaacatgc aaacaggcag gtacatgtcc    4320
acctgacatt ataccctaagg ttgaaggcaa aactattgct gaacaaatat tacaatatgg    4380
aagtatgggt gtattttttg gtgggttagg aattggaaca gggtcgggta caggcggacg    4440
cactgggtat attccattgg gaacaaggcc tcccacagct acagatacac ttgctcctgt    4500
aagaccccct ttaacagtag atcctgtggg cccttctgat ccttctatag tttctttagt    4560
ggaagaaact agttttattg atgctggtgc accaacatct gtaccttcca ttcccccaga    4620
tgtatcagga tttagtatta ctacttcaac tgataccaca cctgctatat tagatattaa    4680
taatactgtt actactgtta ctacacataa taatcccact ttcactgacc catctgtatt    4740
gcagcctcca acacctgcag aaactggagg gcattttaca ctttcatcat ccactattag    4800
tacacataat tatgaagaaa ttcctatgga tacatttatt gttagcacaa accctaacac    4860
agtaactagt agcacaccca taccagggtc tcgcccagtg gcacgcctag gattatatag    4920
tcgcacaaca caacaggtta aagttgtaga ccctgctttt gtaaccactc ccactaaact    4980
tattacatat gataatcctg catatgaagg tatagatgtg gataatacat tatatttttc    5040
tagtaatgat aatagtatta atatagctcc agatcctgac tttttggata tagttgcttt    5100
acataggcca gcattaacct ctaggcgtac tggcattagg tacagtagaa ttggtaataa    5160
acaaacacta cgtactcgta gtggaaaatc tataggtgct aaggtacatt attattatga    5220
tttaagtact attgatcctg cagaagaaat agaattacaa actataacac cttctacata    5280
tactaccact tcacatgcag cctcacctac ttctattaat aatggattat atgtatattta    5340 tgcagatgac tttattacag atacttctac aaccccggta ccatctgtac cctctacatc    5400
tttatcaggt tatattcctg caaatacaac aattccttttt ggtggtgcat acaatattcc    5460
tttagtatca ggtcctgata tacccattaa ataaactgac caagctccctt cattaattcc    5520 tatagttcca gggtctccac aatatacaat tattgctgat gcaggtgact tttattttaca    5580 tcctagttat tacatgttac gaaaacgacg taaacgttta ccatatttt ttcagatgt      5640 ctctttggct gcctagtgag gccactgtct acttgcctcc tgtcccagta tctaaggttg    5700
taagcacgga tgaatatgtt gcacgcacaa acatatatta tcatgcagga acatccagac    5760
tacttgcagt tggacatccc tattttccta ttaaaaaacc taacaataac aaaatattag    5820
ttcctaaagt atcaggatta caatacaggg tatttagaat acatttacct gaccccaata    5880
agtttggttt tcctgacacc tcatttata atccagatac acagcggctg gtttgggcct    5940
```

-continued

```
gtgtaggtgt tgaggtaggt cgtggtcagc cattaggtgt gggcattagt ggccatcctt    6000
tattaaataa attggatgac acagaaaatg ctagtgctta tgcagcaaat gcaggtgtgg    6060
ataatagaga atgtatatct atggattaca aacaaacaca attgtgttta attggttgca    6120
aaccacctat aggggaacac tggggcaaag gatccccatg taccaatgtt gcagtaaatc    6180
caggtgattg tccaccatta gagttaataa acacagttat tcaggatggt gatatggttc    6240
atactggctt tggtgctatg gactttacta cattacaggc taacaaaagt gaagttccac    6300
tggatatttg tacatctatt tgcaaatatc cagattatat taaaatggtg tcagaaccat    6360
atggcgacag cttattttt tatttacgaa gggaacaaat gtttgttaga catttattta    6420
atagggctgg tactgttggt gaaaatgtac cagacgattt atacattaaa ggctctgggt    6480
ctactgcaaa tttagccagt tcaaattatt ttcctacacc tagtggttct atggttacct    6540
ctgatgccca aatattcaat aaaccttatt ggttacaacg agcacagggc cacaataatg    6600
gcatttgttg gggtaaccaa ctatttgtta ctgttgttga tactcacgc agtacaaata    6660 tgtcattatg tgctgccata tctacttcag aaactacata taaaaatact aactttaagg    6720
agtacctacg acatggggag gaatatgatt tacagtttat ttttcaactg tgcaaaataa    6780
ccttaactgc agacgttatg acatacatac attctatgaa ttccactatt ttggaggact    6840
ggaattttgg tctacaacct cccccaggag gcacactaga agatacttat aggtttgtaa    6900
cccaggcaat tgcttgtcaa aaacatacac ctccagcacc taaagaagat gatcccctta    6960
aaaaatacac tttttgggaa gtaaatttaa aggaaaagtt ttctgcagac ctagatcagt    7020 ttccttttagg acgcaaattt ttactacaag caggattgaa ggccaaacca aaatttacat    7080
taggaaaacg aaaagctaca cccaccacct catctacctc tacaactgct aaacgcaaaa    7140
aacgtaagct gtaagtattg tatgtatgtt gaattagtgt tgtttgttgt gtatatgttt    7200
gtatgtgctt gtatgtgctt gtaaatatta agttgtatgt gtgtttgtat gtatggtata    7260
ataaacacgt gtgtatgtgt ttttaaatgc ttgtgtaact attgtgtcat gcaacataaa    7320
taaacttatt gtttcaacac ctactaattg tgttgtggtt attcattgta tataaactat    7380
atttgctaca tcctgttttt gttttatata tactatattt tgtagcgcca ggcccatttt    7440
gtagcttcaa ccgaattcgg ttgcatgctt tttggcacaa aatgtgtttt tttaaatagt    7500
tctatgtcag caactatggt ttaaacttgt acgtttcctg cttgccatgc gtgccaaatc    7560
cctgttttcc tgacctgcac tgcttgccaa ccattccatt gttttttaca ctgcactatg    7620
tgcaactact gaatcactat gtacattgtg tcatataaaa taaatcacta tgcgccaacg    7680
ccttacatac cgctgttagg cacatattt tggcttgttt taactaacct aattgcatat    7740
ttggcataag gtttaaactt ctaaggccaa ctaaatgtca ccctagttca tacatgaact    7800
gtgtaaaggt tagtcataca ttgttcattt gtaaaactgc acatgggtgt gtgcaaaccg    7860
attttgggtt acacatttac aagcaactta tataataata ctaa                    7904
```

METHODS AND MATERIALS FOR TREATING HUMAN PAPILLOMAVIRUS INFECTIONS

CROSS-REFERENCE TO RELATED APPLICATIONS

This application is a National Stage application under 35 U.S.C. §371 that claims the benefit of PCT/US03/20340, filed 26 Jun. 2003, which claims the benefit of U.S. Provisional Application Ser. No. 60/449,066, filed 21 Feb. 2003; U.S. Provisional Application Ser. No. 60/417,997, filed 14 Oct. 2002; and U.S. Provisional Application Ser. No. 60/391,795, filed 26 Jun. 2002.

STATEMENT AS TO FEDERALLY SPONSORED RESEARCH

Funding for the work described herein was provided by the federal government, which may have certain rights in the invention.

BACKGROUND

1. Technical Field

The invention relates to methods and materials involved in treating human papillomavirus infections and human papillomavirus-associated conditions.

2. Background Information

Human Papillomaviruses (HPV), members of the papillomavirinea family of viruses, are recognized as a human pathogen. Various types of HPV are tropic for cutaneous and mucosal epithelial cells, and consequently they are involved in development of papillomas (including common, genital, and planter warts), and cervical carcinomas (zur Hausen, _Curr. Top. Microbiol. Immunol._, 186:131-56 (1994)). Types 16, 18, 31, 33, 35, 39, 45, 52, and 58 are involved in nearly 100 percent of all carcinomas of the cervix (Walboomers et al., _J. Pathol._, 189:12-9 (1999)), with 16 and 18 constituting "high risk" types.

SUMMARY

The invention provides methods and materials related to treating HPV infections (e.g., HPV infections of cutaneous and mucosal epithelial cells) and HPV-associated conditions (e.g., cervical dysplasias (also referred to as cervical intraepithelial neoplasias), HPV-associated cervical carcinomas, oral mucosal papilloma cancers, and laryngeal papilloma cancers). For example, the invention provides (1) methods for treating a mammal having cells infected with HPV, (2) antisense molecules, small interfering RNA (siRNA) molecules, DNAzymes (Dz), and ribozymes (Rz) having a sequence complementary to HPV sequences (e.g., RNA), (3) methods for making antisense molecules, siRNA molecules, Dz, and Rz having a sequence complementary to HPV sequences, (4) methods for obtaining a library of single-stranded Dz, (5) methods for identifying HPV target sequences, (6) methods for treating HPV infections and HPV-associated conditions, and (7) methods and materials for delivering antisense molecules, siRNA molecules, Dz, and Rz to cells infected with HPV.

The invention is based, in part, on the discovery that nucleic acid molecules such as antisense molecules, siRNA molecules, Dz, and Rz can be used successfully to reduce the number of HPV infected cells in a mammal. For example, antisense oligonucleotides (ASO) and Dz designed to interact with HPV E6/E7 RNA can be used to reduce the number of HPV infected cells within a mammal. The HPV infected cells can be cells containing non-integrated HPV nucleic acid and can be exhibiting HPV replication. As described herein, nucleic acid molecules were successfully used to reduce the number of HPV infected cells in a mammal. For example, library selection protocols were developed and used to identify accessible sites in E6/E7 target RNA from HPV11, an HPV type implicated in causation of genital warts. ASO, Rz, and Dz were designed to contain sequences complementary to the identified sites. In addition, the ASO, Rz, and Dz were tested in cell culture. Further, ASO and Dz were used topically to treat HPV11-infected human foreskin grafted onto immunodeficient mice. Topical administration of ASO and Dz resulted in a reduction in the development of HPV infections. In addition, an ASO targeting a site, which had been identified in two different library selection protocols, exhibited the greatest efficacy. For example, antisense molecules targeted to the region surrounding one of the library-selected sites (e.g., nucleotide 407) proved extremely effective in blocking development of HPV11-induced papillomas in human foreskin grafts on immunodeficient mice. The results provided herein demonstrate that molecular therapeutics (e.g., antisense molecules, siRNA molecules, Rz, and Dz) can be used to treat bona fide HPV infections in vivo.

In general, the invention features a method of treating HPV infection comprising administering an effective amount of a nucleic acid molecule to a patient in need thereof wherein the nucleic acid molecule inhibits expression associated with HPV replication. The inhibition can be at any level (e.g., 5, 10, 15, 20, 25, 30, 35, 40, 45, 50, 55, 60, 65, 70, 75, 80, 85, 90, 95, or more percent inhibition). The HPV can be HPV11, HPV16, HPV18, HPV31, HPV33, HPV35, HPV39, HPV45, HPV52, or HPV58. The nucleic acid molecule can be complementary to a nucleic acid sequence of the HPV. The nucleic acid molecule can be administered topically. The nucleic acid molecule can be administered topically to a portion of the genital organ of the patient. The nucleic acid molecule can be administered topically to cervical tissue of the patient. The nucleic acid molecule can be an antisense oligonucleotide or an siRNA molecule. The nucleic acid molecule can be a ribozyme or DNAzyme. The nucleic acid molecule can be administered together with a keratolytic agent, wherein the keratolytic agent can be present in an amount effective to enhance the penetration of the nucleic acid molecule. The keratolytic agent can be salicylic acid or one or more alpha hydroxy acids. The patient can suffer from cervical intraepithelial dysplasia (CIN). The CIN can be CIN I or mild dysplasia. The CIN can be CIN II or moderate to marked dysplasia. The CIN can be CIN III or severe dysplasia to carcinoma-in-situ. The carcinoma-in-situ can be localized to the intraepithelial tissue or the superficial layer of the cervix. The nucleic acid molecule can be identified using a library selection technique. The library selection technique can be an antisense oligonucleotide library selection technique, a ribozyme library selection technique, or a DNAzyme library selection technique.

In another embodiment, the invention features a method for treating a mammal having cells infected with HPV. The method includes administering a nucleic acid molecule to the mammal under conditions wherein the number of the cells infected with the HPV is reduced, wherein the nucleic acid molecule contains a sequence complementary to a nucleotide sequence of the HPV. The mammal can be a non-human, immunodeficient mammal, and the cells can be human cells. The mammal can be a nude or SCID mouse. The mammal can be a human. The cell can be a skin cell or epithelial cell. The HPV can be HPV11, HPV16, HPV18, HPV31, HPV33, HPV35, HPV39, HPV45, HPV52, or HPV58. The nucleic acid molecule can be administered topically to the mammal. The nucleic acid molecule can be administered topically to a portion of the genital organ of the mammal. The nucleic acid molecule can be administered topically to cervical tissue of the mammal. The nucleic acid molecule can be an antisense oligonucleotide or an siRNA molecule. The nucleic acid molecule can be a ribozyme or DNAzyme. The number of the cells infected with the HPV can be reduced by at least 25 percent, at least 50 percent, or at least 75 percent. The nucleotide sequence can contain a target site identified using a library selection technique. The library selection technique can be an antisense oligonucleotide library selection technique, a ribozyme library selection technique, or a DNAzyme library selection technique. The cells infected with the HPV can contain non-integrated HPV nucleic acid. The cells infected with the HPV can contain replicating HPV.

In another aspect, the invention features an isolated catalytic nucleic acid containing a catalytic core sequence, a 5' recognition sequence, and a 3' recognition sequence, wherein the isolated catalytic nucleic acid cleaves a target mRNA sequence selected from the group consisting of the sequences set forth in SEQ ID NOs:4-48. The isolated catalytic nucleic acid can be a ribozyme. The catalytic core sequence can contain the sequence set forth in SEQ ID NO:51. The isolated catalytic nucleic acid can be a DNAzyme. The catalytic core sequence can contain the sequence set forth in SEQ ID NO:68.

In another embodiment, the invention features an isolated, single-stranded nucleic acid molecule consisting of between five and 40 nucleotides, wherein the nucleic acid molecule contains a sequence complementary to at least five consecutive nucleotides of a sequence selected from the group consisting of SEQ ID NOs:4-48. The nucleic acid molecule can be DNA.

Another embodiment of the invention features an isolated, double-stranded RNA molecule, wherein one strand of the RNA molecule contains a nucleic acid sequence complementary to at least five consecutive nucleotides of a sequence selected from the group consisting of SEQ ID NOs:4-48. The RNA molecule can consist of between five and 40 nucleotides. The RNA molecule can consist of between 18 and 25 nucleotides.

Another aspect of the invention features a method for making a library of single-stranded DNAzymes. The method include (a) amplifying nucleic acid in an amplification reaction to form an amplification reaction product, wherein the amplification reaction contains template nucleic acid and a primer containing at least one ribose nucleotide, wherein one strand of the template nucleic acid contains the library of single-stranded DNAzymes, and wherein the amplification reaction product contains double-stranded nucleic acid with a strand containing the at least one ribose nucleotide, (b) contacting the amplification reaction product with a base hydrolysis agent under conditions wherein the strand containing the at least one ribose nucleotide becomes shorter than the other strand of the double-stranded nucleic acid, and (c) obtaining the strand from step (b) containing the library of single-stranded DNAzymes based on size. The amplification reaction can further contain a primer lacking ribose nucleotides. The amplification reaction can contain two primers containing at least one ribose nucleotide. The shorter strand of the double-stranded nucleic acid of step (b) can contain the library of single-stranded DNAzymes. The longer strand of the double-stranded nucleic acid of step (b) can contain the library of single-stranded DNAzymes. The base hydrolysis agent can be sodium hydroxide.

Another aspect of the invention features a composition containing a nucleic acid molecule and a keratolytic agent, wherein the nucleic acid molecule contains a sequence complementary to a nucleic acid sequence present in an HPV, and wherein the keratolytic agent is present in an amount effective to enhance penetration of the nucleic acid molecule. The nucleic acid molecule can be an antisense oligonucleotide or an siRNA molecule. The nucleic acid molecule can be a ribozyme or DNAzyme. The keratolytic agent can be salicylic acid.

Another aspect of the invention features a nucleic acid molecule containing $(N)_{n1}$ followed by $(oxygen-carbon-carbon)_{n2}$ followed by $(N)_{n3}$, wherein N is a nucleotide, and wherein the n1, n2, and n3 are integers greater than 0. The n1 can be between 10 and 20. The n2 can be between 3 and 10. The n3 can be between 10 and 20. The $(N)_{n1}$ can be a DNA sequence of 17 consecutive adenosines. The $(N)_{n3}$ can be a 5'-TGTAAAACGACGGCCAG-3' (SEQ ID NO:79) sequence. The nucleic acid molecule can contain a phosphate group between the $(oxygen-carbon-carbon)_{n2}$ and the $(N)_{n3}$.

Another aspect of the invention features a method for making a library of single-stranded DNAzymes. The method includes (a) amplifying nucleic acid in an amplification reaction to form an amplification reaction product, wherein the amplification reaction contains template nucleic acid and a primer containing an $(oxygen-carbon-carbon)_n$ backbone unit, wherein n is an integer greater than 1, wherein one strand of the template nucleic acid contains the library of single-stranded DNAzymes, and wherein the amplification reaction product contains double-stranded nucleic acid wherein the strand extending from the primer is shorter than the other strand of the double-stranded nucleic acid, and (b) obtaining the strand from step (a) containing the library of single-stranded DNAzymes based on size.

Another aspect of the invention features a method for reducing HPV replication in a cell, wherein the method includes contacting the cell with an antisense molecule, siRNA molecule, Dz, or Rz having sequence specificity for HPV RNA.

In another aspect, the invention features a method for inhibiting development of HPV in a mammal (e.g., human). The method includes (a) identifying via a library selection technique one or more target sites on HPV RNA that are accessible to antisense oligonucleotides, DNAzymes, or ribozymes; (b) designing one or more antisense oligonucleotides, siRNA molecules, DNAzymes, or ribozymes that are at least partially complementary to all or a portion of one or all of the target sites identified in step (a); and (c) contacting the mammal with one or more of the antisense oligonucleotides, siRNA molecules, DNAzymes, or ribozymes designed in step (b) such that development of HPV in the mammal is inhibited.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 contains three panels related to the LS3 method. Panel A is a diagram of a PCR reaction used to generate double-stranded DNA, where one strand contains a library of Dz. The TS-17 (SEQ ID NO:1) and BS-17 (SEQ ID NO:2) primers are labeled. The amplified template (SEQ ID NO:3) contains the primer sequences and random nucleotide stretches flanking a catalytic core sequence (underlined). Panel B is a photograph of a sequencing gel of the PCR products of the Dz library. Panel C is a schematic of several amplification reactions using primers containing a ribose nucleotide ($TS_R$ and $BS_R$) and 2-deoxyribose ($TS_D$ and $BS_D$) primers. The thick lines pointing to the right represent strands containing active Dz sequences.

FIG. 8A is a photograph of a gel used to quantify the levels of HPV16 E6/E7 RNA in cells transfected with $SNIP_{AA}$sRz constructs expressing the indicated Rz. The "AA" denotes an empty $SNIP_{AA}$ cassette (i.e., containing no E6/E7-targeted trans-acting Rz). FIG. 8B is a bar graph plotting the relative HPV16 E6/E7 mRNA levels in cells transfected with $SNIP_{AA}$sRz constructs expressing the indicated Rz. An empty $SNIP_{AA}$ cassette was used as control. FIG. 8C is a bar graph plotting the relative HPV16 E6/E7 mRNA levels in cells transfected with $SNIP_{AA}$sRz constructs expressing the indicated Rz. An empty $SNIP_{AA}$ cassette was used as control. mRz59 and mRz427 denote $SNIP_{AA}$ constructs containing catalytically inactive versions of Rz59 and Rz427, respectively. I Rz denotes an irrelevant $SNIP_{AA}$ construct containing a trans-acting Rz targeted to hepatitis B virus (Pan et al., *RNA*, 7:610-621 (2001)), and pVAX1 denotes the vector control.

FIG. 9A is a schematic of an Rz and Dz interacting with target RNA. The Rz and Dz cleavage sites are identified with an arrow. The numbering of Rz and Dz nucleotides that interact with the target RNA flanking the cleavage site are labeled as N 1 through 5 and Q 1 through 5. FIG. 9B is a photograph of a gel used to measure the amount of target RNA cleavage for various mutant Rz and Dz. The specific mutations are described in Table 4.

FIG. 10A is a bar graph plotting the relative level of HPV16 mRNA in cells containing the following nucleic acid one day after transfection (CMV promoter). Column 1: $p1CLIP_S$/$HPV16_{C+50-68+GUU}$; Column 2: $p1CLIP_{AS}$/$HPV-16_{C+68-50+GUU}$; Column 3: PSIR/$HPV16si_{C+50-68+GUU}$; Column 4: $p1CLIP_{HP}$/$HPV16_{C+50-68+GUU}$; Column 5: $pSIR_{HP}$/$HPV16_{C+50-58+GUU}$; Column 6: $p2CLIP_{HP}$/$HPV16_{C+50-68+GUU}$; Column 7: $p2CHOP_{HP}$/$HPV-16_{C+50-68+GUU}$; Column 8: $pSNIP_{HP}$/$HPV16_{C+50-68+GUU}$; Column 9: $p2CLIP_{HR}$/$HPV16_{C+50-68+GUU}$; Column 10: p2CHOPHR/$HPV16_{C+50-68+GUU}$; Column 11: $pSNIP_{HR}$/$HPV16_{C+50-68+GUU}$; and Column 12: pSNIP (empty cassette). FIG. 10B is a bar graph plotting the relative level of HPV16 mRNA in cells containing the following nucleic acid two days after transfection (U6 promoter). Column 1: $p1CLIP_S$/$HPV16_{C+50-68+GUU}$; Column 2: $p1CLIP_{AS}$/$HPV16_{C+68-50+GUU}$; Column 3: pSIR/$HPV-16si_{C+50-68+GUU}$; Column 4: $p1CLIP_{HP}$/$HPV-16_{C+50-68+GUU}$; Column 5: $pSIR_{HP}$/$HPV16si_{C+50-68+GUU}$; Column 6: $p2CLIP_{HR}$/$HPV16_{C+50-68+GUU}$; Column 7: $p2CHOP_{HR}$/$HPV16_{C+50-68+GUU}$; Column 8: $p2SNIP_{HR}$/$HPV16_{C+50-68+GUU}$; Column 9: pSNIP cassette containing sRa59; and Column 10: pSNIP (empty cassette).

DETAILED DESCRIPTION

Figure 1:
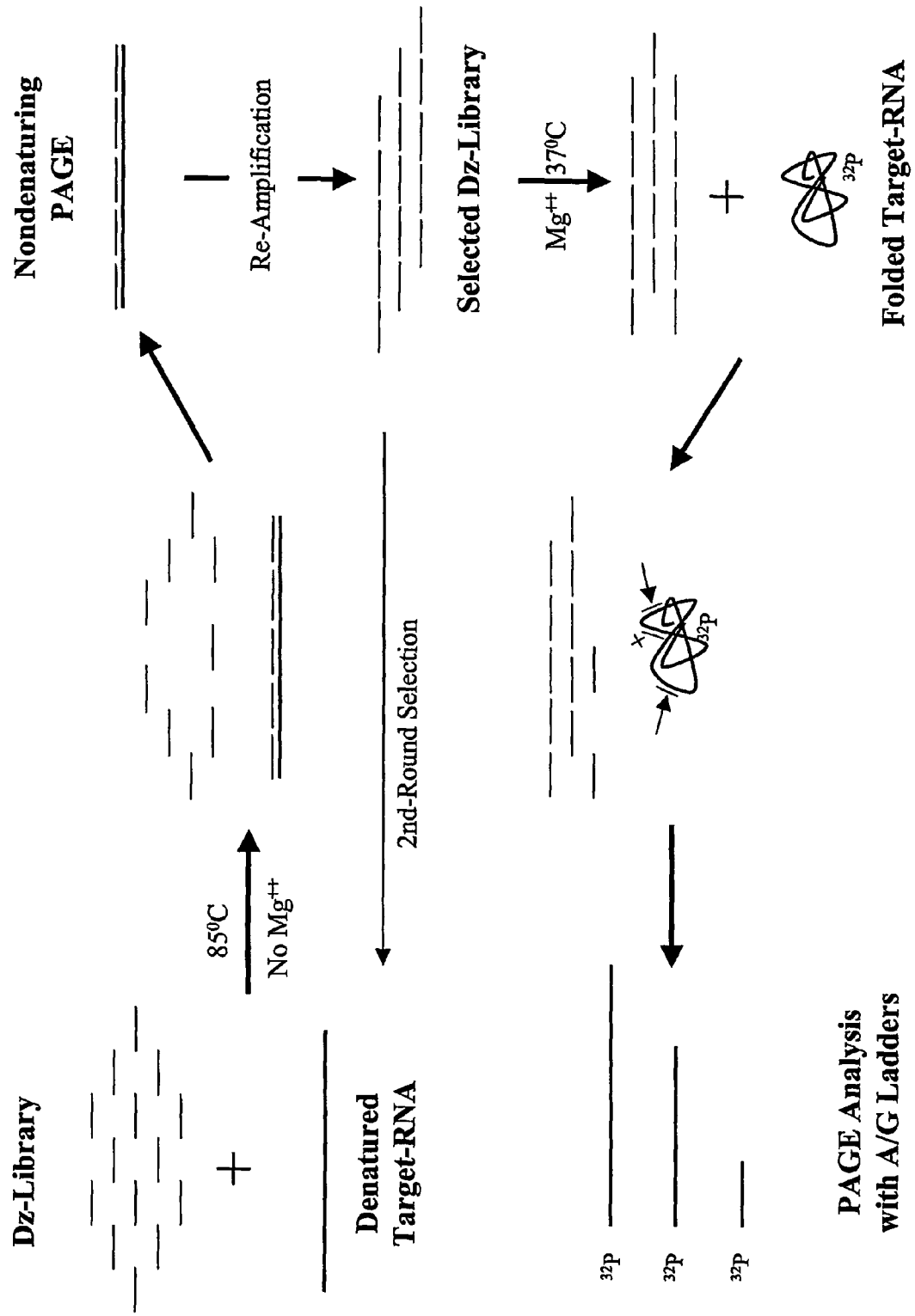
FIG. 1 is a schematic overview of the LS3 (Dz selection library) method.

The invention provides methods and materials related to treating HPV infections and HPV-associated conditions. For example, the invention provides methods for treating mammals (e.g., humans) having cells (e.g., human cells) infected with HPV. The cells can be any type of cell such as skin cells or epithelial cells. In addition, the cells infected with HPV can be located anywhere within the mammal. For example, the HPV-infected cells can be located on the genital organ of the mammal. In some cases, the HPV-infected cells can form part of a genital wart or a cervical dysplasia. The HPV-infected cells also can contain integrated or non-integrated HPV nucleic acid. For example, the HPV-infected cells can contain HPV nucleic acid sequences that integrated into the genome of the cells. In some cases, the HPV-infected cells can lack HPV nucleic acid sequences in their genome. In these cases, HPV nucleic acid sequences can be maintained within the cells episomally. The HPV-infected cells also can exhibit HPV replication. For example, HPV-infected cells can be producing HPV particles.

Mammals having cells infected with any type of HPV can be treated as described herein. For example, humans having cells infected with HPV type 11, 16, 18, 31, 33, 35, 39, 45, 52, or 58 can be treated. In addition, mammals having cells infected with combinations of different HPV types can be treated as described herein. For example, a human having cells infected with both HPV16 and HPV18 can be treated.

As described herein, mammals having cells infected with HPV can be treated using nucleic acid molecules. The term "nucleic acid" as used herein encompasses both RNA and DNA, including cDNA, genomic DNA, and synthetic (e.g., chemically synthesized) DNA. The nucleic acid can be double-stranded or single-stranded. In addition, nucleic acid can be circular or linear. In some embodiments, the nucleic acid can be a plasmid. The nucleic acid can contain one or more restriction sites.

Typically, mammals having cells infected with HPV are treated using nucleic acid molecules that contain a sequence complementary to a nucleic acid sequence of the HPV. For example, antisense molecules, RNA molecules that induce RNA interference (e.g., double stranded RNA molecules, hairpin loop RNA molecules, siRNA molecules, or constructs designed to express such molecules), Rz, or Dz can be designed to have a sequence complementary to an HPV sequence. Such nucleic acid molecules can be complementary to any HPV sequence including, without limitation, non-coding HPV nucleic acid sequences (e.g., poly(A) signal sequences and regulatory sequences such as the upstream regulatory region) and HPV polypeptide-encoding nucleic acid sequences (e.g., E1, E2, E3, E4, E5, E6, E7, L1, and L2 polypeptide-encoding sequences). In some cases, the nucleic acid molecules are designed based on accessible HPV RNA target sites. Such target sites can be identified using any method such as the library selection methods described herein (e.g., LS1, LS2, and LS3). In addition, any method can be used to make nucleic acid molecules such as antisense molecules, RNA molecules that induce RNA interference (e.g., double stranded RNA molecules, hairpin loop RNA molecules, siRNA molecules, or constructs designed to express such molecules), Rz, or Dz having a sequence complementary to an HPV sequence. For example, the methods and materials described in International Patent Application No. PCT/US01/46178 and U.S. Provisional Patent Application No. 60/449,066 can be used.

The term "complementary" as used herein with reference to two nucleic acid sequences (e.g., a Rz or Dz recognition sequence and an HPV mRNA target sequence; or an antisense oligonucleotide sequence and an HPV mRNA target sequence) means the two nucleic acid sequences are 100 percent complementary. The complementary sequences can be part of larger nucleic acid molecules having sequences that are not complementary. The length of the complementary sequence can be any length greater than 3 nucleotides (e.g., 4, 5, 6, 7, 8, 9, 10, 11, 12, 13, 14, 15, 16, 17, 18, 19, 20, 21, 22, 23, 24, 25, 26, 27, 28, 29, 30, or more nucleotides). For example, a 60-nucleotide Dz can have a 10-nucleotide sequence complementary to an HPV mRNA sequence. Typically, complementary sequences range in length from about 4 nucleotides to about 20 nucleotides (e.g., from about 5 nucleotides to about 18 nucleotides, or from about 6 nucleotides to about 15 nucleotides).

Any method can be used to administer a nucleic acid molecule to a mammal containing cells infected with HPV. For example, administration can be topical (e.g., transdermal, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection), or can occur over a period of time (e.g., by slow infusion or administration of slow release formulations).

Typically, when treating a mammal having cells infected with HPV, the nucleic acid molecules are administered topically. For example, nucleic acid molecules formulated with or without liposomes can be topically applied directly to $HPV^+$ precancerous cervical dysplasia tissue or HPV lesions such as genital warts. For topical administration, a nucleic acid molecule can be formulated into compositions such as sterile and non-sterile aqueous solutions, non-aqueous solutions in common solvents such as alcohols, or solutions in liquid or solid oil bases. Such solutions also can contain buffers, diluents, and other suitable additives. Compositions for topical administration can be formulated in the form of transdermal patches, ointments, lotions, creams, gels, drops, suppositories, sprays, liquids, and powders. Coated condoms, gloves, and the like also can be used. Conventional pharmaceutical carriers, aqueous, powder or oily bases, thickeners, and the like can be added.

For oral administration, a nucleic acid molecule can be formulated into compositions such as powders or granules, suspensions or solutions in water or non-aqueous media, capsules, sachets, or tablets. Such compositions also can incorporate thickeners, flavoring agents, diluents, emulsifiers, dispersing aids, or binders.

For parenteral, intrathecal, or intraventricular administration, a nucleic acid molecule can be formulated into compositions such as sterile aqueous solutions, which also can contain buffers, diluents, and other suitable additives (e.g., penetration enhancers, carrier compounds, and other pharmaceutically acceptable carriers).

In addition, nucleic acid molecules can be administered to a mammal containing HPV-infected cells using biologic or abiologic means as described in, for example, U.S. Pat. No. 6,271,359. Abiologic delivery can be accomplished by a variety of methods including, without limitation, (1) loading liposomes with a nucleic acid molecule provided herein and (2) complexing a nucleic acid molecule with lipids or liposomes to form nucleic acid-lipid or nucleic acid-liposome complexes. The liposome can be composed of cationic and neutral lipids commonly used to transfect cells in vitro. Cationic lipids can complex (e.g., charge-associate) with negatively charged nucleic acids to form liposomes. Examples of cationic liposomes include, without limitation, lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including Lipofectin® (Invitrogen/Life Technologies, Carlsbad, Calif.) and Effectene™ (Qiagen, Valencia, Calif.). In addition, systemic delivery methods can be optimized using commercially available cationic lipids such as DDAB or DOTAP, each of which can be mixed with a neutral lipid such as DOPE or cholesterol. In some cases, liposomes such as those described by Templeton et al. (*Nature Biotechnology*, 15:647-652 (1997)) can be used. In other embodiments, polycations such as polyethyleneimine can be used to achieve delivery in vivo and ex vivo (Boletta et al., *J. Am Soc. Nephrol.* 7: 1728 (1996)). Additional information regarding the use of liposomes to deliver nucleic acids can be found in U.S. Pat. No. 6,271,359.

Biologic delivery can be accomplished by a variety of methods including, without limitation, the use of viral vectors. For example, viral vectors (e.g., adenovirus and herpesvirus vectors) can be used to deliver nucleic acid molecules to skin cells and cervical cells. Standard molecular biology techniques can be used to introduce one or more of the nucleic acid molecules provided herein into one of the many different viral vectors previously developed to deliver nucleic acid to cells. These resulting viral vectors can be used to deliver the one or more nucleic acid molecules to cells by, for example, infection.

Nucleic acid molecules having a sequence complementary to an HPV sequence can be formulated in a pharmaceutically acceptable carrier or diluent. A "pharmaceutically acceptable carrier" (also referred to herein as an "excipient") is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

In addition, nucleic acid molecules having a sequence complementary to an HPV sequence can be formulated into compositions containing the nucleic acid molecule admixed, encapsulated, conjugated, or otherwise associated with other molecules, molecular structures, or mixtures of nucleic acids. For example, a composition containing one or more nucleic acid molecules having a sequence complementary to an HPV sequence can contain other therapeutic agents such as anti-inflammatory drugs (e.g., nonsteroidal anti-inflammatory drugs and corticosteroids) and antiviral drugs (e.g., ribivirin, vidarabine, acyclovir, and ganciclovir). In some embodiments, a composition can contain one or more nucleic acid molecules having a sequence complementary to an HPV sequence in combination with a keratolytic agent. Keratolytic agents are agents that separate or loosen the horny layer of the epidermis. An example of a keratolytic agent includes, without limitation, salicylic acid. Other examples are provided in U.S. Pat. No. 5,543,417. Keratolytic agents can be used in an amount effective to enhance the penetration of nucleic acid molecules, for example, into tissues such as skin. For example, a keratolytic agent can be used in an amount that allows a nucleic acid molecule applied to a genital wart to penetrate throughout the wart.

In addition, nucleic acid molecules can be administered in amounts and for periods of time that vary depending upon the age, weight, and condition of the mammal, the nature of the particular HPV infection and its severity, the mammal's overall condition, and the particular compound delivered. Typically, a nucleic acid molecule can be administered in an inhibitory amount such as an amount that inhibits expression of an HPV polypeptide (e.g., E6 or E7 polypeptide). The inhibition can be at any level of inhibition. For example, HPV polypeptide expression can be inhibited by 5, 10, 20, 25, 30, 35, 40, 45, 50, 55, 60, 65, 70, 75, 80, 85, 90, 95, or more percent. In some cases, the inhibition can result in an absence of detectable HPV polypeptide expression. Dosing can be based on the severity and responsiveness of the disease state to be treated, with, for example, the course of treatment lasting from several days to several months, or until a cure is effected or a diminution of the disease state is achieved. Routine methods can be used to determine optimum dosages, dosing methodologies, and repetition rates. Optimum dosages can vary depending on the relative potency of individual nucleic acid molecules, and can generally be estimated based on $EC_{50}$ values found to be effective in in vitro and/or in vivo models. Typically, a dosage is from about 0.01 µg to about 100 g per kg of body weight, and can be given once or more daily, weekly, or even less often. Following successful treatment, it may be desirable to have the patient undergo maintenance therapy to prevent the recurrence of the disease state.

As described herein, nucleic acid molecules having a sequence complementary to an HPV sequence can be administered to a mammal under conditions wherein the number of cells infected with the HPV is reduced. This reduction can be any detectable level of reduction. For example, the number of HPV-infected cells can be reduced by 5, 10, 20, 25, 30, 35, 40, 45, 50, 55, 60, 65, 70, 75, 80, 85, 90, 95, or more percent. In some cases, the reduction can result in an absence of detectable HPV-infected cells.

The presence or absence of HPV-infected cells can be determined using any method. For example, Southern blots, PCR, Northern blots, RT-PCR, immunostaining, ELISAs, and radioimmunoassays can be used to detect HPV DNA, RNA, or polypeptides in a cellular sample. In addition, any method can be used to determine the number of HPV-infected cells within a mammal. For example, standard molecular biology techniques such as in situ hybridization and immunostaining can be used to determine the number of HPV-infected cells. Likewise, any method can be used to determine whether or not the number of HPV-infected cells within a mammal was reduced. For example, tissues can be examined macroscopically, microscopically, immunologically, biochemically, or molecularly before and after treatment to determine whether the number of HPV-infected cells was reduced. Typically, a macroscopically observable size reduction or disappearance of a genital wart (known to contain HPV-infected cells) following treatment indicates that the number of HPV-infected cells was reduced.

The invention also provides isolated nucleic acids. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, lentivirus, adenovirus, or herpes virus), or the genomic DNA of a prokaryote or eukaryote.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The isolated nucleic acids provided herein can be RNA or DNA and can contain one or more catalytic core sequences. The term "catalytic core sequence" as used herein refers to a sequence that is primarily responsible for the catalytic activity of a Dz or Rz, as opposed to target recognition. Examples of catalytic core sequences include, without limitation, SEQ ID NO:51 and SEQ ID NO:68. Other catalytic core sequences are described elsewhere (Santoro and Joyce, *Proc. Natl. Acad. Sci.*, 94(9):4262-6 (1997); Feldman and Sen, *Mol. Biol.*, 313(2):283-94 (2001); and Okumoto et al., *Biochemistry*, 42(7):2158-65 (2003)).

In addition to one or more catalytic core sequences, an isolated nucleic acid provided herein can contain one or more recognition sequences. Typically, a recognition sequence is a sequence complementary to a target sequence such as a target HPV mRNA sequence. In some embodiments, the isolated nucleic acid can contain a 5' recognition sequence followed by a catalytic core sequence followed by a 3' recognition sequence. The recognition sequences can be complementary to any HPV sequence such as an HPV E6/E7 mRNA sequence. The isolated nucleic acids can be designed such that they cleave a cleavage site of an HPV mRNA. Examples of HPV mRNA cleavage sites accessible to Dz and Rz cleavage can be found in Tables 1a, 1b, and 1c.

The invention also provides isolated, single-stranded nucleic acid molecules. Such nucleic acid molecules can consist of between 5 and 40 nucleotides (e.g., between 6 and 35 nucleotides, between 7 and 30 nucleotides, between 8 and 25 nucleotides, or between 8 and 20 nucleotides). In addition, these nucleic acid molecules can have a sequence complementary to at least five consecutive nucleotides (e.g., at least 6, 7, 8, 9, 10, 11, 12, 13, 14, 15, 16, 17, 18, 19, 20, 21, 22, 23, 24, 25, or more consecutive nucleotides) of an HPV mRNA sequence. For example, an isolated, single-stranded nucleic acid molecule provided herein can have a sequence complementary to at least five consecutive nucleotides of the sequences set forth in Tables 1a, 1b, and 1c.

In addition, the invention provides isolated, double-stranded RNA molecules. Typically, one strand of such RNA molecules contains a sequence complementary to at least five consecutive nucleotides (e.g., at least 6, 7, 8, 9, 10, 11, 12, 13, 14, 15, 16, 17, 18, 19, 20, 21, 22, 23, 24, 25, or more consecutive nucleotides) of an HPV mRNA sequence. For example, an isolated, double-stranded RNA molecule provided herein can have a strand having a sequence complementary to at least five consecutive nucleotides of the sequences set forth in Tables 1a, 1b, and 1c.

In some embodiments, the isolated, double-stranded RNA molecules can be designed to be siRNA molecules. Typically, siRNA molecules are short, double-stranded RNA molecules. In addition, siRNA molecules can be any length (e.g., 15, 16, 17, 18, 19, 20, 25, 30, 35, 40, or more nucleotides in length). For example, siRNA molecules can be 15 to 30 nucleotides in length (e.g., 18 to 25, 20 to 24, or 20 to 21 nucleotides in length). In some embodiments, the selected target sequences from HPV RNA can be used to design siRNA molecules. For example, the antisense molecules provided herein can be synthesized as double-stranded RNA molecules. In addition, the length of the siRNA molecules can be identical to the length of the antisense molecules provided herein or the length can be increased or decreased (e.g., the length can be increased or decreased such that the siRNA molecules are 20 to 21 nucleotides in length). Any method can be used to deliver siRNA molecules to cells. For example, siRNA molecules can be applied to cells using the methods described herein for the antisense molecules. Alternatively, a sequence encoding an siRNA molecule can be incorporated into an expression construct that can be introduced into cells so that siRNA molecules are expressed.

The invention also provides methods and materials for obtaining single-stranded DNA (e.g., Dz). Such methods and materials can be used to make libraries of single-stranded Dz. For example, an amplification reaction (e.g., PCR reaction) can be performed using a labeled primer (e.g., a biotin-labeled primer) such that one strand of the resulting double-stranded nucleic acid contains the label. Once amplified, the amplification products can be incubated with a binding agent (e.g., streptavidin) that interacts with the label, allowing the labeled strand to be separated from unlabeled strands. For example, streptavidin-coated resin can be used to remove biotin-containing strands from strands lacking biotin. Typically, the amplification reactions can be designed using primers such that the strand containing Dz sequences (e.g., a library of different Dz sequences) is unlabeled and the complement strand is labeled, for example, with biotin. In this case, the Dz strands can be obtained by collecting material that does not bind to a binding agent resin, for example, streptavidin-coated beads.

Single-stranded DNA also can be obtained using amplification reactions with one or more primers containing one or more ribose nucleotides. The ribose nucleotide or nucleotides can be located anywhere along the primer. Typically, at least one ribose nucleotide is located at or near the 3' end of the primer. Once amplified, the resulting double-stranded nucleic acid can have one strand that contains one or more ribose nucleotides. Treatment of this resulting product with a base hydrolysis agent such as sodium hydroxide can result in cleavage of the strand containing a ribose nucleotide at the ribose nucleotide. Typically, the amplification products are treated with NaOH with a final NaOH concentration of, for example, about 0.1, 0.25, 0.5, or 0.75 M. In addition, once the sodium hydroxide is added, the mixture can be heated (e.g., to about 80° C., 85° C., 90° C., or 95° C.) for several minutes (e.g., about 5, 10, 15 minutes) and then cooled (e.g., placed on ice).

Once the strand containing at least one ribose nucleotide is cleaved, the mixture can be neutralized by adding, for example, HCl with a final HCl concentration of, for example, about 0.1, 0.25, 0.5, or 0.75 M. The two strands can be separated based on size. For example, PAGE (e.g., an 8 percent denaturing polyacrylamide gel) can be used to separate the shorter cleaved strand from a longer uncleaved strand. The band corresponding to the strand containing Dz sequences can be isolated, and the single-stranded Dz eluted.

Single-stranded DNA also can be obtained using amplification reactions with one or more primers containing a carbon spacer. The carbon spacer can be located anywhere along the primer. During amplification reactions, the polymerase typically is unable to extend beyond the carbon spacer, resulting in one strand being longer than the other. The differentially sized strands can be separated, and the strand containing Dz sequences isolated.

Figure 3:
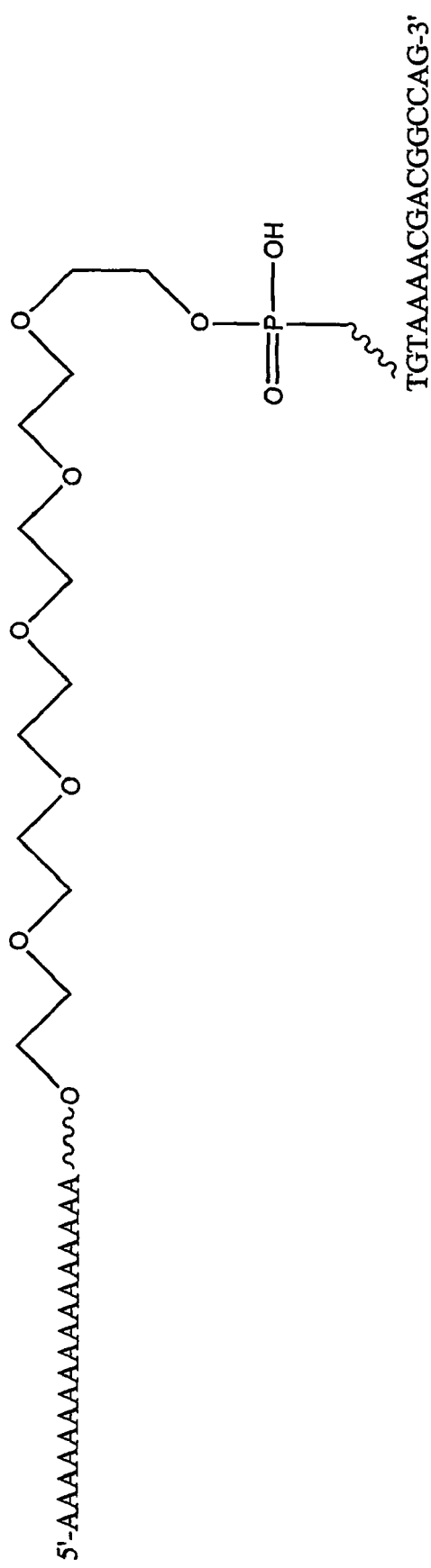
FIG. 3 is a diagram of a nucleic acid molecule containing a carbon spacer.

The term "carbon spacer" as used herein refers to a non-pentose molecular structure that contains one or more carbon-carbon backbone bonds. Typically, a polymerase (e.g., Taq polymerase or a reverse transcriptase) can not polymerize nucleic acid through the carbon spacer region of a template containing a carbon spacer. A carbon spacer can contain repeating oxygen-carbon-carbon units. For example, a carbon spacer can be 2, 3, 4, 5, 6, 7, 8, 9, 10, or more oxygen-carbon-carbon units. In addition, a carbon spacer can contain a phosphate group. For example, six oxygen-carbon-carbon units can be followed by a phosphate group (FIG. 3). Typically, the primer will contain a 5' nucleic acid sequence following by one or more oxygen-carbon-carbon units followed by a phosphate group followed by a 3' nucleic acid sequence. Such primers can contain any nucleic acid sequence.

In some embodiments, the invention provides nucleic acid molecules having a nucleic acid sequence (represented as $(N)_{n1}$, where N is any nucleotide, and n1 is an integer greater than 0) followed by a carbon spacer (e.g., an oxygen-carbon-carbon unit represented as $(oxygen-carbon-carbon)_{n2}$, where n2 is an integer greater than 0) followed by another nucleic acid sequence (represented as $(N)_{n3}$, where N is any nucleotide, and n3 is integer greater than 0). The nucleic acid sequences represented as $(N)_{n1}$ and $(N)_{n3}$ can have any sequence. For example, $(N)_{n1}$ can be 5'-ATGG-3', and $(N)_{n3}$ can be 5'-CTGAC-3'.

The invention will be further described in the following examples, which do not limit the scope of the invention described in the claims.

EXAMPLES

Example 1

Library Selection of Target Sites

Full-length $HPV11_{E6/E7}$, $HPV16_{E6/E7}$, and $HPV18_{E6/E7}$ RNA was transcribed and subjected to library selection using a random pool of oligonucleotides (LS1), a pool of active Rz (LS2) with random flanking sequences, or a pool of active Dz (LS3) with random flanking sequences. Briefly, the LS1 library selection protocol involved using a random oligonucleotide library SELEX procedure (5 rounds) according to Pan et al. (*RNA*, 7:610-21 (2001)). The LS2 library selection was performed using a random library of active Rz (Pan et al., *Mol. Therapy*, 7:128-138 (2003) and International Patent Application No. PCT/US01/46178). Briefly, the library was allowed to bind to target RNA (e.g., $HPV11_{E6/E7}$, $HPV16_{E6/E7}$, or $HPV18_{E6/E7}$ RNA) under inactive conditions, a the bound species were reamplified. A second round of binding and amplification was performed at a lower target RNA: Rz ratio to increase specificity. The selected pool was then transcribed into active Rz that were incubated with full-length 5'-$^{32}$P-$HPV11_{E6/E7}$, $HPV16_{E6/E7}$, or $HPV18_{E6/E7}$ labeled target RNA, Cleavage products were separated on sequencing gels, and sites of cleavage were directly identified by comparison with G-, T-, and base hydrolysis ladders.

The LS3 library selection was performed using a random library of active Dz (FIG. 1; International Patent Application No. PCT/US01/46178). Briefly, a library of single-stranded Dz was prepared and allowed to bind to target RNA (e.g., $HPV11_{E6/E7}$, $HPV16_{E6/E7}$, or $HPV18_{E6/E7}$ RNA) under inactive conditions (85° C. and no $Mg^{++}$), and the bound species were obtained by nondenaturing PAGE and reamplified. A second round of binding and amplification was performed at a lower target RNA:Dz ratio to increase specificity. Single-stranded Dz were obtained from the selected pool and incubated with full-length 5'-$^{32}$P-$HPV11_{E6/E7}$, $HPV16_{E6/E7}$, or $HPV18_{E6/E7}$ labeled target RNA under active conditions (37° C. and 25 mM MgCl). Cleavage products were separated on sequencing gels, and sites of cleavage were directly identified by comparison with G-, T-, and base hydrolysis ladders. Both one and two rounds of selection using the LS3 protocol resulted in detectable cleavage. These results indicate that accessible cleavage sites can be identified using one round of selection with the LS3 protocol, although sites are more readily apparent after two rounds of selection.

During the LS3 protocol, the single-stranded Dz were obtained using a PCR reaction where a biotin-labeled primer was used to prime the strand lacking the Dz sequence. A streptavidin-containing resin was then used to separate the biotin-labeled strand from the Dz-containing strand. Alternatively, ribose-containing primers (e.g., DNA primers where the base at the 3' end is a ribose) were used to perform amplification reactions that resulted in one strand containing an RNA nucleotide (FIG. 2). Sodium hydroxide (0.5 M final concentration) was added to the amplification reaction product to cleave the strand containing the ribose nucleotide between the ribose and 2-deoxyribose nucleotides. After adding sodium hydroxide, the mixture was incubated at 95° C. for 10 minutes and then placed on ice. The resulting mixture was neutralized with HCl, and the two strands separated based on size using an 8 percent denaturing polyacrylamide gel. The band corresponding to the strand containing the Dz sequence was isolated, and the single-stranded Dz were eluted. A third method involved using a primer that contained a carbon spacer. The carbon spacer contained repeating oxygen-carbon-carbon units followed by a phosphate group (FIG. 3). During amplification reactions, the polymerase is unable to extend beyond the carbon spacer, resulting in one strand being longer than the other. The differentially sized strands were then separated, and the strand containing the Dz sequences isolated.

A number of sites were identified with each protocol (Tables 1a and 1b). In addition, several sites were identified using both the LS1 and LS2 protocols (e.g., a site surrounding nucleotide position 407 of $HPV11_{E6/E7}$ RNA, which corresponds to nucleotide position 505 in Genbank® accession number M14119; Table 1b). HPV target sequences were also selected without a library selection protocol. For example, several sites within E5 close to a common poly(A) signal used for the majority of HPV transcripts were selected (Table 1c).

TABLE 1a

HPV target sequences identified using library selection protocols and used to make Rz.

| Target mRNA | Genbank ® Accession Number | Rz | Cleavage Site | Library Selection Protocol | Target Sequence |
|---|---|---|---|---|---|
| HPV16 E6/E7 | K02718 | 31 | 110 | LS1 | UGCAAUG<u>UUU</u>CAGGACC (SEQ ID NO:4) |
| | | 59 | 138 | LS2 | CCCAGAAA<u>GUU</u>ACCACA (SEQ ID NO:5) |

TABLE 1a-continued

HPV target sequences identified using library selection protocols and used to make Rz.

| Target mRNA | Genbank ® Accession Number | Rz | Cleavage Site | Library Selection Protocol | Target Sequence |
|---|---|---|---|---|---|
| | | 68 | 147 | LS2 | UUACCACAGUUAUGCAC (SEQ ID NO:6) |
| | | 150 | 229 | LS2 | GAGGUGAGGUAUAUGAC (SEQ ID NO:7) |
| | | 187 | 266 | LS2 | CAUAGUAUAUAGAGAUG (SEQ ID NO:8) |
| | | 251 | 330 | LS2 | AUUAGUGAGUAUAGACA (SEQ ID NO:9) |
| | | 275 | 354 | LS2 | UAUAGUUUGUAUGGAAC (SEQ ID NO:10) |
| | | 358 | 437 | LS1 | GCCACUGUGUCCUGAAG (SEQ ID NO:11) |
| | | 415 | 494 | LS2 | UAUAAGGGGUCGGUGGA (SEQ ID NO:12) |
| | | 427 | 506 | LS1/LS2 | GUGGACCGGUCGAUGUA (SEQ ID NO:13) |
| HPV11 E6/E7 | M14119 | 23 | 121 | LS1 | AAAGAUGCCUCCACGUC (SEQ ID NO:14) |
| | | 162 | 260 | LS2 | ACCUAAAGGUUGUGUGG (SEQ ID NO:15) |
| | | 244 | 342 | LS2 | UAGACACUUUAAUUAUG (SEQ ID NO:16) |
| | | 345 | 443 | LS1 | UGUGUGAAAUAGAAAAA (SEQ ID NO:17) |
| | | 409 | 507 | LS1/LS2 | GUGGAAGGGUCGUUGCU (SEQ ID NO:18) |
| | | 449 | 547 | LS2 | GAAGACUUGUUACCCUA (SEQ ID NO:19) |
| | | 499 | 597 | LS2 | CCUGUAGGGUUACAUUG (SEQ ID NO:20) |
| | | 529 | 627 | LS2 | GAAGACAGCUCAGAAGA (SEQ ID NO:21) |
| | | 593 | 691 | LS2 | AUUACCAAAUACUGACC (SEQ ID NO:22) |
| HPV18 E6/E7 | X05015 | 19 | 123 | LS1 | CUUUGAGGAUCCAACAC (SEQ ID NO:23) |
| | | 340 | 444 | LS1 | ACCGUUGAAUCCAGCAG (SEQ ID NO:24) |
| | | 403 | 507 | LS1 | UGGGCACUAUAGAGGCC (SEQ ID NO:25) |

The underlined nucleotides represent Rz cleavage sites.

TABLE 1b

HPV target sequences identified using library selection protocols and used to make Dz.

| Target mRNA | Genbank ® Accession Number | Dz | Cleavage Site | Library Selection Protocol | Target Sequence |
|---|---|---|---|---|---|
| HPV16 E6/E7 | K02718 | 57 | 136 | LS2 | CCCAGAAAGTTACCACA (SEQ ID NO:26) |
| | | 66 | 145 | LS2 | TTACCACAGTTATGCAC (SEQ ID NO:27) |
| | | 148 | 227 | LS2 | GACGTGAGGTATATGAC (SEQ ID NO:28) |
| | | 185 | 264 | LS2 | CATAGTATATAGAGATG (SEQ ID NO:29) |
| | | 249 | 328 | LS2 | ATTAGTGAGTATAGACA (SEQ ID NO:30) |
| | | 273 | 352 | LS2 | TATAGTTTGTATGGAAC (SEQ ID NO:31) |
| | | 413 | 492 | LS2 | TATAAGGGGTCGGTGGA (SEQ ID NO:32) |
| | | 425 | 504 | LS1/LS2 | GTGGACCGGTCGATGTA (SEQ ID NO:33) |

TABLE 1b-continued

HPV target sequences identified using library
selection protocols and used to make Dz.

| Target mRNA | Genbank® Accession Number | Dz | Cleavage Site | Library Selection Protocol | Target Sequence |
|---|---|---|---|---|---|
| | | 589 | 668 | LS3 | GGAGGAGGATGAAATAG (SEQ ID NO:34) |
| HPV11 E6/E7 | M14119 | 27 | 125 | LS1 | GCCTCCACGTCTGCAAC (SEQ ID NO:35) |
| | | 160 | 258 | LS2 | ACCTAAAGGTTGTGTGG (SEQ ID NO:36) |
| | | 231 | 329 | LS2 | ATTAACCAATATAGACA (SEQ ID NO:37) |
| | | 323 | 421 | LS2 | TTACCTGTGTCACAAGC (SEQ ID NO:38) |
| | | 338 | 436 | LS1 | GCCGTTGTGTGAAATAG (SEQ ID NO:39) |
| | | 407 | 505 | LS1/LS2 | GTGGAAGGGTCGTTGGT (SEQ ID NO:40) |
| | | 447 | 545 | LS2 | GAAGACTTGTTACCCTA (SEQ ID NO:41) |
| | | 526 | 624 | LS2 | AGAAGACAGCTCAGAAG (SEQ ID NO:42) |
| | | 591 | 689 | LS2 | ATTACCAAATACTGACC (SEQ ID NO:43) |
| HPV18 E6/E7 | X05015 | 17 | 121 | LS1 | CTTTGAGGATCCAACAC (SEQ ID NO:44) |
| | | 338 | 442 | LS1 | ACCGTTGAATCCAGCAG (SEQ ID NO:45) |
| | | 401 | 505 | LS1 | TGGGCACTATAGAGGCC (SEQ ID NO:46) |

The bold nucleotides represent Dz cleavage sites.

TABLE 1c

HPV target sequences within E5 close to a common
poly(A) signal used for the majority of HPV
transcripts.

| Target mRNA | Genbank® Accession Number | Dz | Cleavage Site | Target Sequence |
|---|---|---|---|---|
| HPV16 E6/E7 | K02718 (SEQ ID NO:85) | AA3916 | 3916 | GTGCTTTTGTGTGTCTG (SEQ ID NO:47) |
| | | AA4015 | 4015 | GGCTCTGCGTTTAGGTG (SEQ ID NO:48) |

The bold nucleotides represent Dz cleavage sites.

Example 2

Design of ASO, Rz, and Dz

ASO, Rz, and Dz were designed to target sites identified using the library selection protocols. For example, ASO407$_{(HPV11-E6/E7)}$ was designed to bind to the region surrounding 409 (Table 1a) and has the following sequence: 5'-AGCAACGACCCTTCCAC-3' (SEQ ID NO:49). A protected version of ASO407$_{(HPV11-E6/E7)}$, ASO407$_{p(HPV11-E6/E7)}$, was designed to have the following sequence: 5'-AGCAACGACCCTTCCAC-T*-3' (SEQ ID NO:50). The "T*" indicates that the thymidine is inverted (Santiago et al., *Nat. Med.*, 5(11):1264-69 (1999)). As described below, this modification significantly protected the ASO and Dz against degradation in medium/serum and in cells.

Five Rz, Rz23$_{(HPV11-E6/E7)}$, Rz162$_{(HPV11-E6/E7)}$, Rz244$_{(HPV11-E6/E7)}$, Rz345$_{(HPV11-E6/E7)}$, and Rz409$_{(HPV11-E6/E7)}$, were designed to have a catalytic core sequence (e.g., 5'-CUGAUGAGUCCGUGAGGACGAAA-3'; SEQ ID NO:51) flanked by sequences complementary to the target site sequences. For example, Rz59$_{(HPV16-E6/E7)}$, designed to cut cleavage site 138 of HPV16 E6/E7 RNA, can have the following sequence: 5'-UGUGGUCUGAUGAG-UCCGUGAGGACGAAACUUUCUGGG-3' (SEQ ID NO:52) where the underlined sequence represents the catalytic core sequence. The Rz cut sites were chosen within the accessible regions according to Rz specificity considerations (e.g., NUC triplet for Rz).

The template sequence for each Rz was placed in a SNIP$_{AA}$ expression cassette (FIG. 5A) either as single internal transacting Rz (ITRz) or as double ITRz (dITRz). Briefly, this cassette consists of two triple Rz (Zhang et al., *Exp. Cell Res.*, 273:73-84 (2002)). Each of the triple ribozymes, in turn, consists of two cis-acting ribozymes flanking the ITRz or dITRz. The two cis-acting Rz cleave the primary transcript, liberating the ITRz or dITRz with minimal extraneous flanking sequences. Use of this cassette provides an additional advantage in that the liberated ITRz or dITRz is distributed between nucleus (5-20%) and cytoplasm (Pan et al., *RNA*, 7:610-21 (2001); Benedict et al., *Carcinogenesis*, 19:1223-30 (1998); Ren et al., *Gene Therapy and Mol. Biol.*, 3:1-13 (1998); and Crone et al., *Hepatology*, 29:1114-23 (1999)).

The ITRz or dITRz liberated from the CLIP portion of the SNIP$_{AA}$ cassette contained a flanking sequence at the 5' end (5'-AGCUCGACCUCAGAUCU-3'; SEQ ID NO:53) and at the 3' end (5'-CAAUUGAAAAAAAAAAAAAAAAAAAA-AAAAAAAAAAAGUC-3'; SEQ ID NO:54). The ITRz or dITRz liberated from the CHOP portion of the SNIP$_{AA}$ cassette contained a flanking sequence at the 5' end (5'-GGUUC-CAGGAUCC-3'; SEQ ID NO:55) and at the 3' end (5'-GAA-UUCAAAAAAAAAAAAAAAAAAAAAAAAAAAAAA-AGUC-3'; SEQ ID NO:56). The "catalytic core" of the various ITRz and dITRz Rz consisted of the following sequence: 5'-CUGAUGAGUCCGUGAGGACGAAA-3' (SEQ ID NO:51). The flanking sequences were as follows for the indicated ITRz:

```
Rz162:
   ---CCACAC-"Catalytic Core"-CCUUUAGGU---     (SEQ ID NO:57)

Rz244:
   ---CAUAAU-"Catalytic Core"-AAGUGUCUA---     (SEQ ID NO:58)

Rz409:
   ---AGCAAC-"Catalytic Core"-CCCUUCCAC---     (SEQ ID NO:59)
```

The flanking sequences were as follows for the indicated dITRz:

```
Rz409/162:   ---AGCAAC-"Catalytic Core"-CCCUUCCAC-CCACAC-"Catalytic Core"-AAGTGTCTA---    (SEQ ID NO:60)

Rz409/244:   ---AGCAAC-"Catalytic Core"-CCCUUCCAC-CAUAAU-"Catalytic Core"-AAGUGUCUA---    (SEQ ID NO:61)

Rz409/409:   ---AGCAAC-"Catalytic Core"-CCCUUCCAC-AGCAAC-"Catalytic Core"-CCCUUCCAC---    (SEQ ID NO:62)
```

In addition, the ITRz409 from the CLIP portion of the SNIP$_{AA}$ cassette contained the following sequence: 5'-AGCUCGACCUCAGAUCUAGCAACCUGAUGAGU-CCGUGAGGACGAAACCCUUCCACCAAUUGAAAA-AAAAAAAAAAAAAAAAAAAAAAAAGUC-3' (SEQ ID NO:63). The HPV11-specific flanking sequences are underlined. The dITRz409/409 from the CLIP portion of the SNIP$_{AA}$ cassette contained the following sequence: 5'-AGCUCGACCUCAGAUCUAGCAACCUGAUGAGU-CCGUGAGGACGAAACCCUUCCACAGCAACCUGA-UGAGUCCGUGAGGACGAAACCCUUCCACCAAUU-GAAAAAAAAAAAAAAAAAAAAAAAAAAAAAAAG-UC-3' (SEQ ID NO:64). Again, the HPV11-specific flanking sequences are underlined.

Dz27$_{(HPV11-E6/E7)}$, Dz338$_{(HPV11-E6/E7)}$, and Dz407$_{(HPV11-E6/E7)}$ were designed cut sites identified with the LS1 protocol, since Dz targeted to sites identified with the LS2 protocol can exhibit poor activity. The Dz cut sites were chosen within the accessible regions according to Dz specificity considerations (e.g., an R-Y doublet for Dz). Dz27$_{(HPV11-E6/E7)}$, which targets cleavage site 125 of HPV11 E6/E7 RNA, was designed to have the following sequence: 5'-GTTGCAGAGGCTAGCTACAACGAGTGGAGGC-3' (SEQ ID NO:65). Dz338$_{(HPV11-E6/E7)}$, which targets cleavage site 436 of HPV11 E6/E7 RNA, was designed to have the following sequence: 5'-CTATTTCAGGCTAGCTACAAC-GAACAACGGC-3' (SEQ ID NO:66). Dz407$_{(HPV11-E6/E7)}$, which targets cleavage site 505 of HPV11 E6/E7 RNA, was designed to have the following sequence: 5'-AGCAACGA GGCTAGCTACAACGACCTTCCAC-3' (SEQ ID NO:67). In each case, the catalytic core of the Dz is underlined (5'-GGCTAGCTACAACGA-3'; SEQ ID NO:68).

A catalytically inactive Dz targeted to 407 (Dz407m$_{(HPV11-E6/E7)}$) was designed and used as a control. Dz407m$_{(HPV11-E6/E7)}$ has the following sequence: 5'-AG-CAACGAGCCTAGCTACTACGACCTTCCAC-3' (SEQ ID NO:69). The nucleotide substitutions, which eliminate Dz catalytic activity, are shown in bold. DzAR2000 and a catalytically inactive version of DzAR2000, DzAR2000m, were designed to target an androgen receptor RNA sequence and used as controls. DzAR2000 has the following sequence: 5'-TCCGAAGAGGCTAGCTACAACGAGACAAGAT-3' (SEQ ID NO:70). DzAR2000m has the following sequence:

5'-TCCGAAGAGCCTAGCTACTACGAGACAAGAT-3' (SEQ ID NO:71).

Example 3

Analysis of In Vitro Cleavage Activity

Once designed, the Rz and Dz were tested in vitro for activity against E6/E7 target RNA under conditions as described elsewhere (Pan et al., *RNA*, 7:610-21 (2001)). The Rz were obtained by synthesizing overlapping oligodeoxynucleotides, which encoded the ITRz sequence downstream of a 5' T7 promoter. The ITRz (identical to those liberated from the CHOP portion of the SNIP cassette) were then transcribed in vitro and gel purified. The Dz were obtained from DNagency (Malvern, Pa.).

Figure 4:
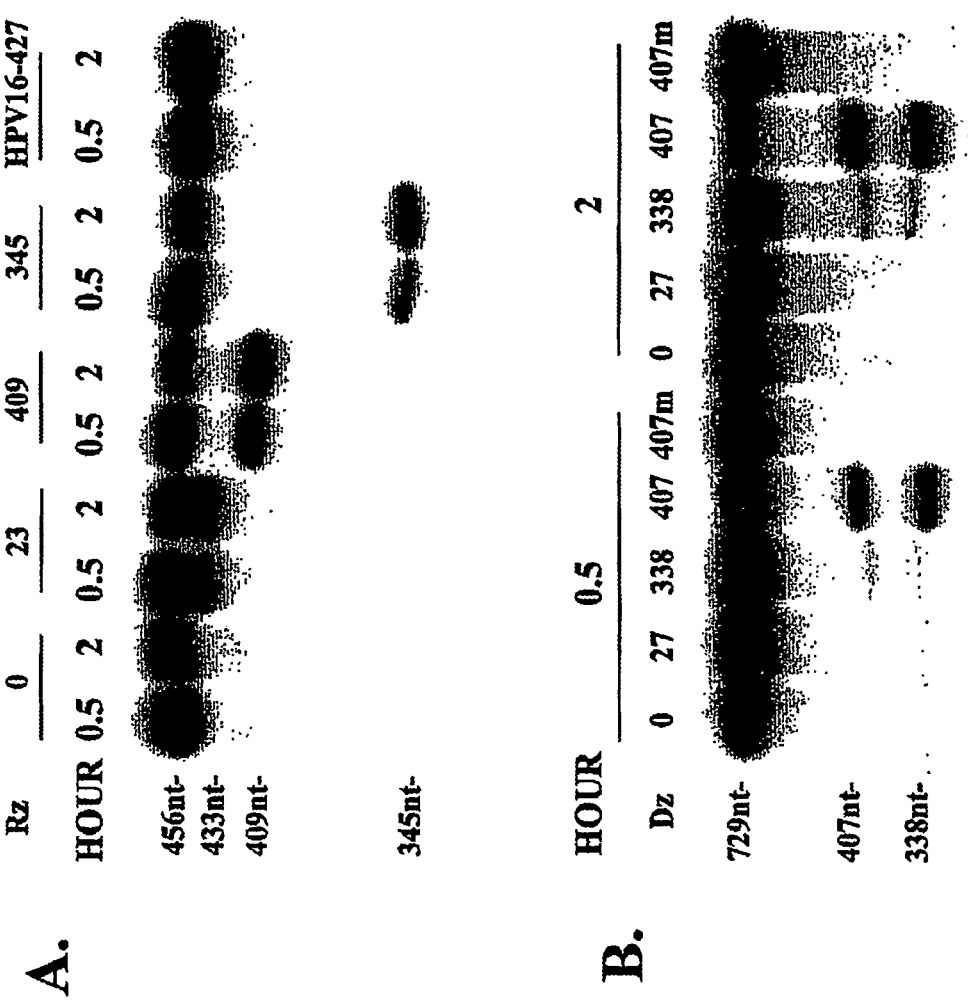
FIG. 4 contains photographs of gels separating cleavage products produced in an in vitro assay using the indicated Rz (A) and Dz (B).

Rz (Rz23$_{(HPV11-E6/E7)}$, Rz409$_{(HPV11-E6/E7)}$, and Rz345$_{(HPV11-E6/E7)}$) were designed based on identified sites, transcribed in vitro, and gel purified. Rz (at 50 nM) were mixed with full length $^{32}$P-labeled HPV11 E6 target mRNA (at 200 nM) and incubated for 30 minutes or 2 hours at 37° C., and the cut products were then examined by PAGE and autoradiography. Rz409$_{(HPV11-E6/E7)}$ and Rz23$_{(HPV11-E6/E7)}$ were the most active Rz (FIG. 4A). The HPV16-targeted Rz (targeted to the homologous region in HPV 16 E6/E7, nucleotide position 427) exhibited no activity against the HPV11 E6 target mRNA. This HPV16 Rz and the HPV11 E6 target mRNA target differ in the $2^{nd}$, $5^{th}$, and $6^{th}$ nucleotides downstream from the cutting site, and in the $5^{th}$ and $6^{th}$ nucleotides upstream. The activity of the HPV16-targeted Rz against an HPV16 E6/E7 target mRNA has a $k_{cat}/k_m$ of $4\times10^5$ min$^{-1}$ M$^{-1}$ with a $K_m$ of about 50 nM. The activity of the Rz409$_{(HPV11-E6/E7)}$ against an HPV11 E6 target mRNA appears similar, although detailed analyses were not performed.

Dz targeted to identified sites exhibited a spectrum of activities against $^{32}$P-labeled HPV11 E6/E7 mRNA. For example, Dz27$_{(HPV11-E6/E7)}$ exhibited no in vitro catalytic activity, Dz338$_{(HPV11-E6/E7)}$ exhibited some in vitro activity, and Dz407$_{(HPV11-E6/E7)}$ exhibited good in vitro activity (FIG. 4B). Interestingly, the 407 site was identified using both LS1 and LS2 protocols. In addition, out of the 12 Dz targeting the 12 sites identified with the LS2 protocol, Dz407$_{(HPV11-E6/E7)}$ was the only Dz showing good activity. The mutant Dz, Dz407m$_{(HPV11-E6/E7)}$, did not exhibit any activity.

Four single-stranded Dz library pools of varying lengths were obtained using an amplification reaction with ribose-containing primers (FIG. 2): (1) Dz plus the TS and BS primer sequences (TS+Dz+BS; 67 nucleotides), (2) Dz plus the TS primer sequence (TS+Dz; 50 nucleotides), (3) Dz plus the BS primer sequence (Dz+BS; 50 nucleotides), and (4) Dz without the primer sequences (Dz; 33 nucleotides). Once obtained, they were tested for in vitro catalytic activity against labeled HPV16 E6/E7 mRNA. All four exhibited detectable cleavage activity at the targeted site. These results indicate that amplification reactions using ribose-containing primers can be used to obtain active Dz. These results also indicate that Dz of varying size can be used to cleave mRNA targets.

Example 4

Cell Culture Analysis of ASO, Rz, and Dz

The following cell culture experiments were performed using 293T human embryonic kidney cells (ATCC, Rockville, Md.; # CRL-1573). The 293T cells were maintained in Dulbecco's Modified Eagles Medium (DMEM) plus 10 percent heat-inactivated bovine calf serum.

In a preliminary stability study, 3'-protected (ASO$_P$) or unprotected ASO were 5'-end labeled with $\gamma^{32}$P-ATP. The 5'-$^{32}$P-labeled ASO$_P$ and unprotected ASO were then incubated for various periods in medium (DMEM plus 10 percent heat-inactivated bovine calf serum). 5'-$^{32}$P-labeled ASO$_P$ and unprotected ASO also were transfected into 293T cells, and RNA was isolated on days 1, 3, and 5 following transfection.

In medium, no degradation of protected ASO$_P$ was observed at 48 hours. The unprotected ASO, however, exhibited about 70 to 80 percent degradation at 48 hours. After transfection into 293T cells, ASO$_P$ exhibited about three to five times more stability at day 5 than the degree of stability observed with unprotected ASO.

Cells stably expressing HPV11 E6/E7 mRNA were generated as follows. 293T cells were stably transfected using the Flp-In system (Invitrogen). The Flp-In 293T cells were grown in the presence of zeocin (400 μg/mL) to maintain the FRT site, which is used for targeted recombination at a unique site in the genome. An HPV11$_{E6/E7}$ sequence was cloned into a pcDNA5 vector, which was then co-transfected into the Flp-In 293 cells along with pOG44 (a vector that allows expression of the Flp recombinase) using Lipofectamine PLUS reagents. Two days after transfection, the cells were exposed to antibiotic selection with hygromycin B (30 μg/mL). This selected for the integrated pcDNA5/FRT construct. After 30 days, single colonies were picked, and tested for β-galactosidase activity and HPV11$_{E6/E7}$ expression. The stably transfected cells were designated 293T$_{E6/E7}$. For comparative purposes, expression of HPV11$_{E6/E7}$ was about six times greater than that of HPV16$_{E6/E7}$ in CaSki cells.

The 293T$_{E6/E7}$ cells were subsequently transfected with various ASO, SNIP$_{AA}$ Rz constructs, or Dz targeted to HPV11 E6/E7. Transfection efficiencies were estimated to be about 70 to 90 percent. HPV11$_{E6/E7}$ target RNA levels were measured via real-time quantitative PCR (QPCR) using a Stratagene (La Jolla, Calif.) Mx4000 machine and TaqMan 5'-nuclease methodology, with either VIC or 6-carboxy-fluorescein (FAM) and Black Hole Quencher 1 (BHQ). For HPV11$_{E6/E7}$, an initial 3'-primer with reverse complementary to nucleotides 827-803 was used. For QPCR, the 3'-primer was reverse complementary to nucleotides 226-203, and the 5'-primer matched nucleotides 154-175. The TaqMan probe was (FAM)-CTTTCCCTTTGCAGCGTGTGCCTGT-(BHQ) (SEQ ID NO:72), which matched nucleotides 177-201.

mRNA for the ubiquitous transcription factor TATA-box binding protein (TBP, an integral component of TFIID) was used for normalization (Herasse et al., *Mol. Cell Biol.*, 19:4047-55 (1999)). For TBP, the initial 3'-primer (5'-CTG-GAAAACCCAACTTCTGTACAA-3'; SEQ ID NO:73) was reverse complementary to nucleotides 742-718. For QPCR, the same 3'-primer was used. The 5'-primer (5'-ACCACG-GCACTGATTTTCAGT-3'; SEQ ID NO:74) matched nucleotides 625-646. The TaqMan probe ((VIC)-TGTGCACAG-GAGCCAAGAGTGAAGA-(BHQ); SEQ ID NO:75) matched nucleotides 659-683. ROX (carboxy-X-rhodamine, succinimidyl ester) was used as dye for a volume control. In some experiments, 18S ribosomal RNA was also quantified.

RT reactions utilized Sensiscript reverse transcriptase (Qiagen) with 50 ng RNA. Standard curves were generally run with 25-100 ng total RNA. QPCR reactions used HotStar Taq Polymerase (Qiagen). 2 μL of the RT reaction was used in a 20 μL reaction. Amplifications were performed in triplicate, and HPV11$_{E6/E7}$ and TBP were matched from the same RT reactions for each. Initial denaturing was at 95° C. for 15 minutes. Each cycle consisted of 95° C. for 30 seconds, 56° C. for 1 minute, and 72° C. for 30 seconds. The data were analyzed using the REST program and the pair-wise fixed reallocation randomization test (Pfaffl et al., *Nucleic Acids Res.*, 30:e36 (2002)) with TBP as reference. The results were similar without normalization.

Figure 5:
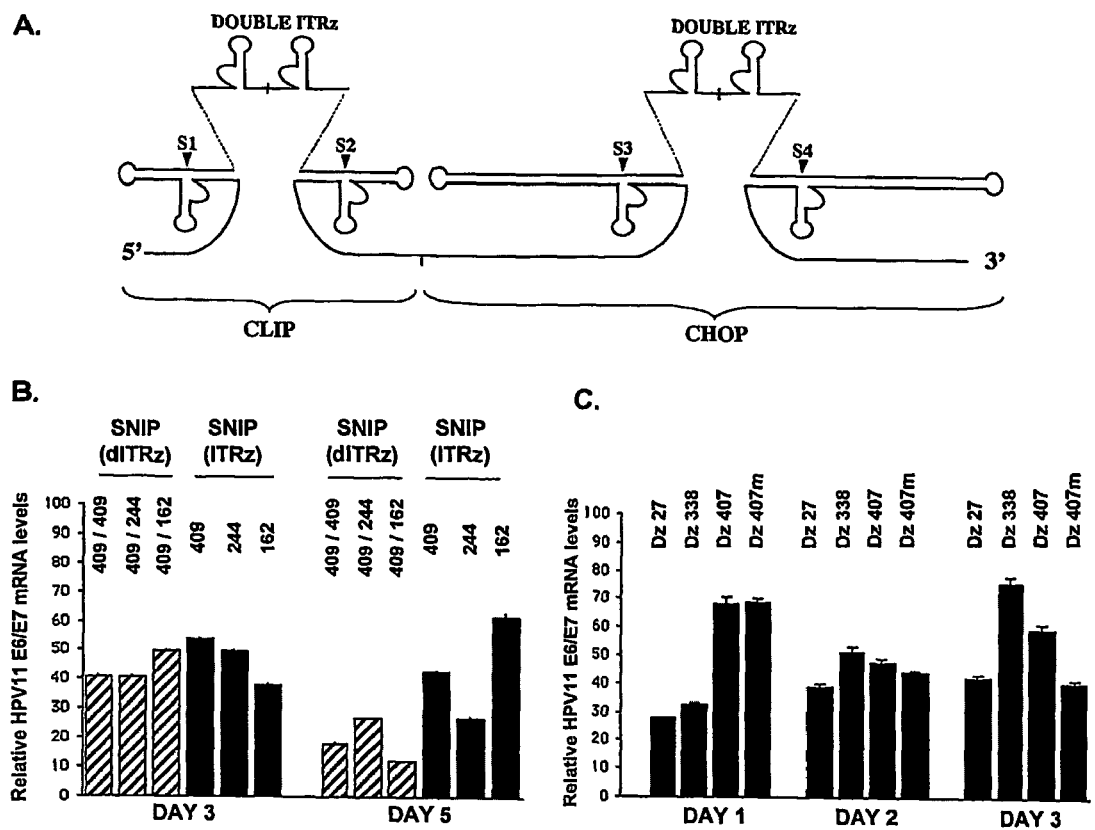
FIG. 5A is a diagrammatic representation of a $SNIP_{AA}$ expression cassette with the CLIP and CHOP portions indicated. S1 and S2 identify the autocatalytic cleavage sites for the cis-acting Rz in CLIP, while S3 and S4 identify the autocatalytic cleavage sites for the cis-acting Rz in CHOP. dITRz are depicted for the liberated trans-acting Rz, although single ITRz can be used instead of dITRz. A poly(A) tract is near the 3'-end of the liberated dITRz or ITRz in the $SNIP_{AA}$ cassette. The CHOP portion contains longer complementary flanking sequences for the cis-acting Rz, which enhances their autocatalytic activity.
FIG. 5B is a bar graph plotting the relative amount of HPV11 E6/E7 mRNA in cells co-transfected with (1) a construct designed to express HPV11 E6/E7 target mRNA and (2) a construct designed to express an ITRz or dITRz targeting the indicated target site.
FIG. 5C is a bar graph plotting the relative amount of HPV11 E6/E7 mRNA in cells stably expressing HPV11 E6/E7 target mRNA and transfected with a Dz designed to target the indicate site.

One day following transfection, minor decreases in HPV11 E6/E7 mRNA levels were observed in cells transfected with SNIP dITRZ (409/409), SNIP dITRZ (409/244), SNIP dITRZ (409/162), SNIP ITRZ (409), SNIP ITRZ (244), and SNIP ITRZ (162). At 3 and 5 days following transfections, significant reductions in HPV11 E6/E7 mRNA were observed (FIG. 5B). By day 5, the SNIP$_{AA}$ Rz constructs containing the dITRz were clearly more effective than those containing a single ITRz, producing reductions in HPV11 E6/E7 mRNA levels of about 80 to 90 percent. The greatest activity appeared to be attributable to Rz409 in a number of experiments. An empty SNIP cassette (i.e., no ITRz) had minor effects, and all SNIP$_{AA}$RZ values differed significantly from control at day 3 and day 5. In various repeat experiments, similar results were obtained.

Cellular RNA was isolated from 293T$_{E6/E7}$ cells at 1, 2, and 3 days following transfection with Dz27$_{(HPV11-E6/E7)}$, Dz338$_{(HPV11-E6/E7)}$, Dz407$_{(HPV11-E6/E7)}$, or Dz407m$_{(HPV11-E6/E7)}$. After 1 day, cells transfected with each Dz constructs exhibited substantial reductions in HPV11E6/E7 target mRNA levels (FIG. 5B). Effects were similar at day 2, with all Dz constructs resulting in 50 to 60 percent reductions in target RNA levels. Effects were diminishing, but still evident, by day 3. The catalytically inactive mutant of Dz407$_{(HPV11-E6/E7)}$, (Dz407m$_{(HPV11-E6/E7)}$) resulted in effects that were equivalent (on day 3, even superior) to those of Dz407$_{(HPV11-E6/E7)}$. In addition, Dz27$_{(HPV11-E6/E7)}$, which is devoid of catalytic activity, resulted in major reductions in target RNA at all 3 time points. These results indicate that the activities observed under these conditions were attributable to antisense effects. Thus, the following in vivo studies included ASO directed to these sites.

Example 4

Preparation of Foreskin and Orthografting

Foreskin fragments were prepared from circumcisions as described elsewhere (Slebos et al., PNAS, 91:5320-4 (1994)). The foreskin was free of detectable lesions and was cut split-thickness (0.5 mm), and then cut into 5×5 mm pieces. These pieces were incubated with 0.2 mL of HPV-11 virus stock (Kreider et al., *J. Virol.*, 61:590-3 (1987)) for 1 hour at 37° C., and then grafted immediately onto 5-10 week old female immunodeficient NIH-III mice (#NIHBNX-MMC, Harlan Laboratories, Indianapolis, Ind.). These mice carry three separate mutations (bg, nu, and xid), which result in deficiencies in T, B, and NK cells. The mice were anesthetized, and a section of epidermis/dermis equivalent to the graft was removed over the rib cage. The graft was then placed in the area and covered with a 1×1 cm nonadherent dressing, which in turn was covered with porous tape wrapped around the mouse. The grafts were then allowed to heal for 10 to 14 days before the bandages were removed. The "take" rate was about 60 percent. Visible papillomas developed about 60 to 70 days following grafting. After infection and grafting of foreskin, the various ASO or Dz were topically applied at the time papillomas became evident macroscopically (i.e., with diameters of 1-2 mm), ensuring that characteristic lesions would develop in each case. Spontaneous regression is not observed in this model. For treatment of grafts, the ASO or Dz were applied topically to developing papillomas in a volume sufficient to cover the surface (e.g., 25 µL, with DNA at 1 µg/µL). Treatment was continued every other day for about 20 to 30 days, at which time the experiments were terminated, and the grafts were processed histology, immunohistochemistry (for E6, E7, or L1 polypeptides), and via in situ hybridization (for HPV11 DNA).

Example 5

Topical Delivery of ASO and Dz

Topical delivery of expression constructs was quite poor, when tested with a variety of delivery vehicles, including cationic liposomes (Templeton et al., *Nature Biotech.*, 15:647-52 (1997)). The delivery of smaller oligonucleotides (e.g., ASO and Dz) was assessed. In initial studies, fluorescein-labeled ASO or Dz were prepared in lipofectamine:ethanol (70:30, v:v) at concentrations of 1 µg or 2 µg/µL. ASO or Dz in lipofectamine:ethanol were applied topically to human foreskin or breast skin grafts, or to the back skin of 5-10 week old female NIH-III mice. Delivery was assessed by fluorescence microscopy at 6, 12, or 24 hours following topical application.

Delivery of fluorescein-labeled ASO to full-thickness xenograft human epidermis and mouse epidermis was excellent using 1 or 2 µg/µL DNA in a 70:30 mixture (v:v) of lipofectamine:ethanol, although it was not possible to document cellular uptake under these conditions. Delivery of fluorescein-labeled Dz was generally similar although somewhat more variable under the same conditions. In some experiments, PBS was used as delivery vehicle, and delivery appeared comparable, although delivery was poor after papillomas had developed.

In another experiment, fluorescein-labeled ASO (10 µL of a 1 µg/µL solution) were topically applied to mouse cervix. Two mice received fluorescein-labeled ASO with a gel foam, and two mice received the fluorescein-labeled ASO without the gel foam. The two mice receiving the ASO without the gel foam and one mouse receiving the ASO with the gel foam were sacrificed four hours after application. In each case, fluorescence was observed through the full-thickening of the cervical epithelium. The remaining mouse receiving the ASO with the gel foam was sacrificed twelve hours after application. In this case, no fluorescence was detected. In addition, no gel foam was detected, indicating that the gel foam may not have been properly applied or retained.

Example 6

In Situ Hybridization and Immunohistochemistry

Cloned HPV11 (8 kbp, Hershey strain) was labeled with Bio-11-dUTP by random priming (Megaprime DNA Labeling System, Amersham, Piscataway, N.J.) according to the manufacturer's instructions. Probes were diluted to 1 µg/mL in a 50% formamide hybridization cocktail (50% formamide in 2.4 M NaCl, 40 mM Tris-HCl, pH 7.4, 2 mM EDTA, 4 mg/mL BSA, 0.08% polyvinylpyrrolidone, 0.08% ficoll, 0.6 mg/mL yeast tRNA, and 80 mM dithiothreitol).

Paraffin sections were dewaxed, dehydrated with ethanol, and then digested with pepsin (4 mg/mL, in 0.1 N HCl). The tissues were then neutralized with 95% ethanol, subsequently dehydrated in 100% ethanol, and then allowed to air dry. The probe cocktail was applied to the tissue, and the tissue and probe combination was denatured at 95° C. for 6 minutes. Hybridization was performed for 2 hours at 37° C. in a moist chamber. The samples were then thoroughly washed in 2×SSC, and the hybridized probe was detected by incubation with an avidin-alkaline phosphatase conjugate, followed by colorimetric development in McGady reagent (nitroblue tetrazolium, 50 mg/mL, and 5-bromo-4-chloro-3-indoyl phosphate, p-toluidine salt, 50 mg/mL, in 50% dimethylformamide). Slides were counterstained with nuclear fast red and cover slipped in permanent mounting medium.

For immunohistochemical detection of E6 and E7 polypeptides, polyclonal antibodies were raised in chickens against three 17-aa polypeptides. The E7 polypeptide was HGRLVTLKDIVLDLQPC (SEQ ID NO:76). The two E6 polypeptides were MESKDASTSATSIDQLC (SEQ ID NO:77) and LELQGKINQYRHFNYAC (SEQ ID NO:78). These polypeptides were synthesized and HPLC purified (Genemed Biotechnologies, South San Francisco, Calif.). They were targeted to regions in HPV11 E6/E7, which were homologous to immunogenic regions previously identified in HPV16 (Stacey et al., *Oncogene*, 9:635-45 (1994)). The polypeptides were coupled to keyhole limpet hemocyanin, and antibodies were induced by immunization of chickens on days 1, 21, 42, and 63 (Cocalico Biologicals, Reamstown, Pa.). After analysis of test bleeds, antiserum collected on day 73 was used, and antibodies were purified using thiophylic adsorption chromatography (T-gel absorbent, Pierce, Rockford, Ill.) according to the manufacturer's specifications. Egg yolks were also obtained, and IgY immunoglobulins were purified from them.

For immunohistochemical staining, paraffin embedded tissues were used. Paraffin sections of cysts developed from HPV11-infected human foreskin, which had been grafted under the renal capsule of athymic mice, were used as a positive control. immunoperoxidase staining was carried out using the avidin-biotin complex method (ABC kits, Vector Laboratories, Austin, Tex.). Sections were deparaffinized and hydrated through xylene and a graded ethanol series. Endogenous peroxidase was quenched using 3% $H_2O_2$ in water for 5 minutes. Blocking was performed with 10% normal goat serum for 30 minutes, following by avidin-biotin blocking. The sections were incubated overnight at 4° C. in a 1:100 dilution of T-gel purified antibodies, with 10% normal goat serum in PBS, followed by 2 washes in PBS. Sections were subsequently incubated for 1 hour in biotinylated secondary goat anti-chicken IgG (8 μg/mL). Nova Red substrate (Vector Laboratories) was used as precipitating substrate for the localization of peroxidase activity, which was then visualized as red reaction product. In some experiments, a rabbit polyclonal antibody directed against HPV11 L1 (from Signet, Dedham, Mass.) was used with a goat anti-rabbit secondary antibody.

For immunoblot analyses, 15% acrylamide gels were used (Laemmli, *Nature*, 227:680-5 (1970)). Nickel-purified histidine-tagged E6 fusion proteins and an HPV11 cyst extract were used as positive controls, and an HPV40 cyst extract was used as a negative control. Following PAGE, separated proteins were transferred to nitrocellulose membrane, and the membrane was blocked in Tween-20/Tris-buffered saline, and incubated with a 1:50 dilution of the antibody preparations in the same buffer. Controls included samples containing 15 μg/mL of the polypeptide used for immunization. Detection was performed using horseradish-peroxidase-linked rabbit anti-chicken IgG (Sigma, St. Louis, Mo.), with 4-chloro-1-naphthol and $H_2O_2$ (each at 0.05%), using methanol as chromogen.

Example 7

Treating HPV Infections

For in vivo studies, a model was used wherein human foreskin, obtained locally from a consortium of hospitals/physicians, was infected with HPV11 and grafted onto NIH-III triple immunodeficient mice (Kreider et al., *J. Virol.*, 61:590-3 (1987)). In this model, papillomas develop and become visible grossly after a characteristic incubation period of about 60 days. After infection and grafting of foreskin, topical application of various ASO or Dz was begun at the time papillomas became evident macroscopically. Treatment was continued every other day for about 20-30 days, at which time the experiments were terminated, and the grafts were processed for histology, immunohistochemistry (for E6, E7, or L1 protein), and via in situ hybridization (for HPV11 DNA). In total, 21 foreskin grafts were treated with $Dz407_{(HPV11-E6/E7)}$ (n=10) and $ASO407_{(HPV11-E6/E7)}$ (n=11; 6 unprotected and 5 protected), excluding various controls.

The largest and most consistent therapeutic responses were observed with $ASO407_{(HPV11-E6/E7)}$, either as a protected (3'-inverted T) or an unprotected ASO (Table 2). In 4 of 11 grafts treated with $ASO407_{(HPV11-E6/E7)}$, a complete therapeutic success was achieved in that no residual papillomatous lesions remained and no residual HPV11 could be detected in the grafts by in situ hybridization. In one graft treated with $ASO407_{(HPV11-E6/E7)}$, no residual HPV11 could be detected by in situ hybridization, although gross evidence of the papilloma remained at the end of treatment. This papilloma had a slight reduction in size (−4% and −12% at 14 and 28 days, respectively) in contrast to grafts with persistent virus, all of which consistently demonstrated increases in papilloma size. Eradication of viral DNA was thus achieved in 5 of 11 grafts treated with $ASO407_{(HPV11-E6/E7)}$ compared to 0 of 6 control grafts. Using Fisher's exact test, there is no significant difference in the proportion of viral negativity between the ASO-treated samples and controls (p=0.10), which presumably reflects the small sample size. In addition to the complete responses, partial responses were observed histologically in the remaining 6 of 11 $ASO407_{(HPV11-E6/E7)}$-treated grafts, consisting of localized reductions in in situ hybridization signal. These, however, were not accompanied by reductions in the size of the papillomas.

TABLE 2

Complete response rates by in situ hybridization (ISH) of treated foreskin grafts.

| Reagent Applied | # grafts ISH Positive | # grafts ISH Negative | Total # grafts | Complete ISH Response Rate (%) |
|---|---|---|---|---|
| $ASOp407_{(HPV11-E6/E7)}$ | 6 | 5 | 11 | 45 |
| $Dz407_{(HPV11-E6/E7)}$ | 7 | 3 | 10 | 30 |

Treatment effects in partial responders appeared to be inversely related to the extent of hyper- and parakeratosis within local regions within the papillomas. In this regard, marked residual viral staining was evident in areas showing the thickest cornification. This result indicates that treatment efficacy can reflect the ability of the ASO to penetrate the keratin layer. There was no clear enhancement of activity with the protected $ASOp407_{(HPV11-E6/E7)}$, in spite of the significant increase in stability observed in vitro. Immunohistochemistry for HPV11 E7 polypeptides also confirmed concurrent loss of E6/E7 polypeptides under these conditions.

In the $Dz407_{(HPV11-E6/E7)}$-treated grafts, 3 of 10 grafts had no evidence of HPV11 DNA using in situ hybridization (Table 2). In each of these cases, however, residual papillomas were observed grossly following treatment, and reductions in gross papilloma size were not noted. Apoptotic cells were often evident, with accumulation of nuclear debris. This response was particularly prominent in samples treated with $Dz407_{(HPV11-E6/E7)}$, and again may reflect partial penetration and/or uptake of Dz, even in areas with relatively little keratinization. This cellular response was often accompanied by a notable loss of koilocytes. In 7 of 10 grafts demonstrating positive in situ hybridization, microscopic effects were variably observed, but were restricted to the upper layers of the epidermis.

Grafts also were treated with $Dz27_{(HPV11-E6/E7)}$, $Dz338_{(HPV11-E6/E7)}$, and $Dz407_{(HPV11-E6/E7)}$. Treatment with $Dz27_{(HPV11-E6/E7)}$ produced slight therapeutic effects, even though Dz27 exhibited no catalytic activity when tested in vitro. This therapeutic effect can be attributed to an antisense effect. Treatment with $Dz338_{(HPV11-E6/E7)}$ produced variable results. In some grafts, a complete blockage of papilloma development was observed. Grafts treated with $Dz407_{(HPV11-E6/E7)}$ also showed partial therapeutic effects.

These studies involved developing and applying library selection protocols to identify accessible sites in HPV target mRNA, namely the E6/E7 biscistronic mRNA. Both the LS1 selection protocol and the LS2 protocol employed iterative binding steps to enrich the libraries for accessible binding regions. LS1 employs a library of random oligonucleotides and identifies sites accessible for binding, whereas LS2 employs a library of random Rz and directly identifies Rz cleavage sites.

The 407/409 cut site region was identified in both LS1 and LS2 protocols. This region is homologous to the nucleotide position 427 region in HPV $16_{E6/E7}$ mRNA, one of the HPV types important in cervical cancer. In HPV$16_{E6/E7}$ mRNA, sites/regions 434 or 437-447 were previously described by others (Alvarez-Salas et al., *Antisense Nucleic Acid Drug Dev.*, 9:441-50 (1999) and Venturini et al., *Nucleic Acids Res.*, 27:1585-92 (1999)). Since different numbering schemes were used, the 434 site identified by others corresponds to site 358 described herein (as a hammerhead ribozyme, Rz358 would cleave after nucleotide 436 in the alternate numbering scheme). Rz358 was in fact identified in an HPV$16_{E6/E7}$ LS1 protocol. In our hands, however, Rz358 activity was slightly less than that of Rz427 in vitro, and Rz427 exhibited superior effects in cell culture. The 427 site in HPV$16_{E6/E7}$ would correspond to nucleotide 505 in the alternate numbering scheme.

As described herein, Dz produced substantial reductions in HPV$11_{E6/E7}$ target RNA in cell culture, in spite of the relatively high target expression levels (and <100% transfection efficiencies). However, since catalytically inactive Dz produced equivalent results, ASO targeted to the selected sites were also included in subsequent testing in vivo.

In addition, ASO and Dz constructs were also tested with 3'-inverted T's as protective groups. The 3'-inverted T constructs showed significantly increased stability in medium and within cells. However, the 3'-inverted T modification did not increase the efficiency of Dz in cell culture under the conditions utilized, and more importantly it had no demonstrable effect on the efficacy of ASO in vivo. Enhanced activity with 3'-inverted T moieties might become apparent at lower doses or with extended intervals between applications.

Papillomas in humans are known to sporadically undergo spontaneous resolution. It is thought that this phenomenon is immunologically-mediated. During the 8-week observation period in studies of genital papillomas treated with imiquimod, 0/57 control lesions underwent spontaneous regression (Beutner et al., *J. Am. Acad. Dermatol.*, 38:230-239 (1998)). During the experiments described herein using the human foreskin graft model, no papillomas exhibited evidence of spontaneous regression during the observation period. This is further supported by the persistence and growth of papillomas in control grafts. Furthermore, since spontaneous regression of papillomas is immunologically-mediated, this phenomenon would not be expected to occur in immunodeficient mice.

Grafts treated with ASO407$_{(HPV11-E6/E7)}$ exhibited the greatest therapeutic efficacy, completely eliminating viral DNA expression in 5 of 11 samples, causing complete regression of papillomas in 4 of these 5. The elimination of viral expression was statistically significant (p<0.02) based on comparison with concurrent and historic foreskin graft controls. This complete response ("cure") rate of 4 of 11 (36%) is comparable to the rate achieved with topical imiquimod and other therapies (Beutner et al., *J. Am. Acad. Dermatol.*, 38:230-239 (1998)). The remaining 7 of 11 grafts (64%) treated with ASO407$_{(HPV11-E6/E7)}$ exhibited partial responses.

Dz407$_{(HPV11-E6/E7)}$, and other less active Dz targeted to other library selected sites, also exhibited a therapeutic efficacy, at least microscopically, in terms of viral eradication and cellular effects. In 3 of 10 grafts, viral DNA expression was abolished, yet gross evidence of the papilloma remained at the end of therapy. It is possible that there may be a lag time between viral eradication and regression of the papilloma. Since the animals were sacrificed at the time the grafts were harvested, this hypothesis was not addressed in these experiments.

The therapeutic effects of Dz in vivo appeared to be restricted to the upper levels of the epidermis, where apoptosis and nuclear debris were observed, as well as absence of koilocytosis. This effect was greatest with Dz407$_{(HPV11-E6/E7)}$, and appeared to be specific, since it was not observed after treatment with irrelevant Dz, DzAR2000. Restriction to the upper levels of epidermis might reflect poorer penetration of Dz as compared to the penetration of ASO (32 nucleotides for protected Dz, 31 nucleotides for unprotected Dz, 18 nucleotides for protected ASO, and 17 nucleotides for unprotected ASO), although this was not clearly supported in topical delivery studies with fluorescein-labeled oligonucleotides, or it might reflect lower cellular uptake of Dz.

The partial responses to eradication of HPV viral DNA observed with both ASO and Dz clearly correlated with the local thickness of the keratin layer. In situ hybridization for HPV11 DNA showed strong staining in areas exhibiting extensive keratinization in residual lesions, and often showed little or no residual staining in areas with little keratinization. The extent of keratinization thus appears to affect penetration, which could contribute to the reduced efficacy in areas of extensive hyperkeratosis. Improved results can be obtained in early papillomas, which are less extensively keratinized. This may not represent an obstacle when treating mucosal surfaces. Alternatively, for nonmucosal skin, these reagents can be combined with a pretreatment aimed at reducing the thickness of the stratum corneum such as the use of topical salicylic acid, paring, or cryotherapy.

The results provided herein demonstrate the successful treatment of HPV-induced lesions. These results also demonstrate that nucleic acid agents such as ASO, siRNA molecules, Rz, and Dz can be used to reduce the number of cells infected with HPV in vivo. In fact, successful targeting of HPV11$_{E6/E7}$ mRNA can block papilloma development in human foreskin, often with elimination of detectable HPV. Efficacy appears to be inversely related to the extent of keratinization, so that clinical applications on nonmucosal skin can be coupled with treatments to reduce and/or eliminate surface cornification prior to (or during) topical delivery.

Example 8

Library Selection of HPV16-E6/E7 Target Sites

A double-stranded DNA library was used to generate an Rz-library with multiple copies of about $10^{10}$ different RNA sequences. Each transcript was 79 nucleotides in length, with a central Rz core flanked on each side by random sequences of 9Ns and by defined 5'- and 3'-end sequences. See, International Patent Application No. PCT/US01/46178. The main purposes of the fixed 5' and 3' sequences were 2-fold: (1) they allow a PCR-based iterative protocol for regeneration of bound species; (2) they substantively decrease (by 20×) the catalytic activity of the active Rz species, which results in identification of Rz that are highly active in subsequent testing; and (3) they facilitate cloning into the SNIP cassette.

DNA templates of targeted RNA were generated by RT-PCR with a T7 promoter in the 5'-primers. To circumvent the problem of microheterogeneity of transcripts at their 3'-ends, a 3'-primer encoding a self-cleaving Rz was used so that transcripts with precise 3'-GUC ends were produced during in vitro runoff transcription.

Incubating the active Rz library with target RNA did not yield cleavage products, due to the huge diversity engineered into the library. To circumvent this, the Rz library was first subjected to selection under magnesium-free conditions, to allow isolation of RNA molecules that annealed to the corresponding target-RNA. The isolated annealed Rz-library RNA pool was subsequently amplified by RT-PCR, and then subjected to a second round of selection at a lower target-RNA ratio, to increase the selection stringency, and to decrease background. The annealing temperature of 85° C. was used to maximize binding of library Rz to all regions of the target RNA during these binding steps. When annealing was performed at 37° C., the procedure did not work. This might be attributable to the lack of magnesium in the incubations.

The re-amplified second round selected Rz (sRz) library RNA pool was used to cleave 5'- or 3'-end labeled target-RNA. The cleaved products were analyzed on sequencing gels, in comparison with G-, A-, and/or base-hydrolysis products, and the cleavage sites were precisely identified. Eleven cleavage sites were located on the HPV16 E6/E7 target RNA. The intensity of the cleaved products generally (but not always) reflected the catalytic activity of that sRz. Occasional anomalous bands were observed, presumably reflecting changes in site accessibility due to interplay between distinct Rz. Without the iterative binding steps, no cleavage of target RNA could be identified.

Within HPV16 E6/E7 RNA, sites/regions 434 (Alvarez-Salas et al., *Proc. Natl. Acad. Sci. (USA)*, 95:1189-1194 (1998)) or 437-447 (Venturini et al., *Nucleic Acids Res.*, 27:1585-1592 (1999)) have been previously described. Given the different numbering schemes, the 434 site identified corresponds to site 358 herein (as an Rz, this would cleave after nucleotide 436 in the alternate numbering scheme). Rz358 was in fact identified in an HPV16 E6/E7 LS1 protocol. In addition, Rz358 activity was slightly less than that of Rz427 in vitro, but Rz427 showed superior effects in cell culture.

Example 9

In Vitro Cleavage Kinetics of sRz Targeting HPV16 E6/E7 mRNA

Figure 6:
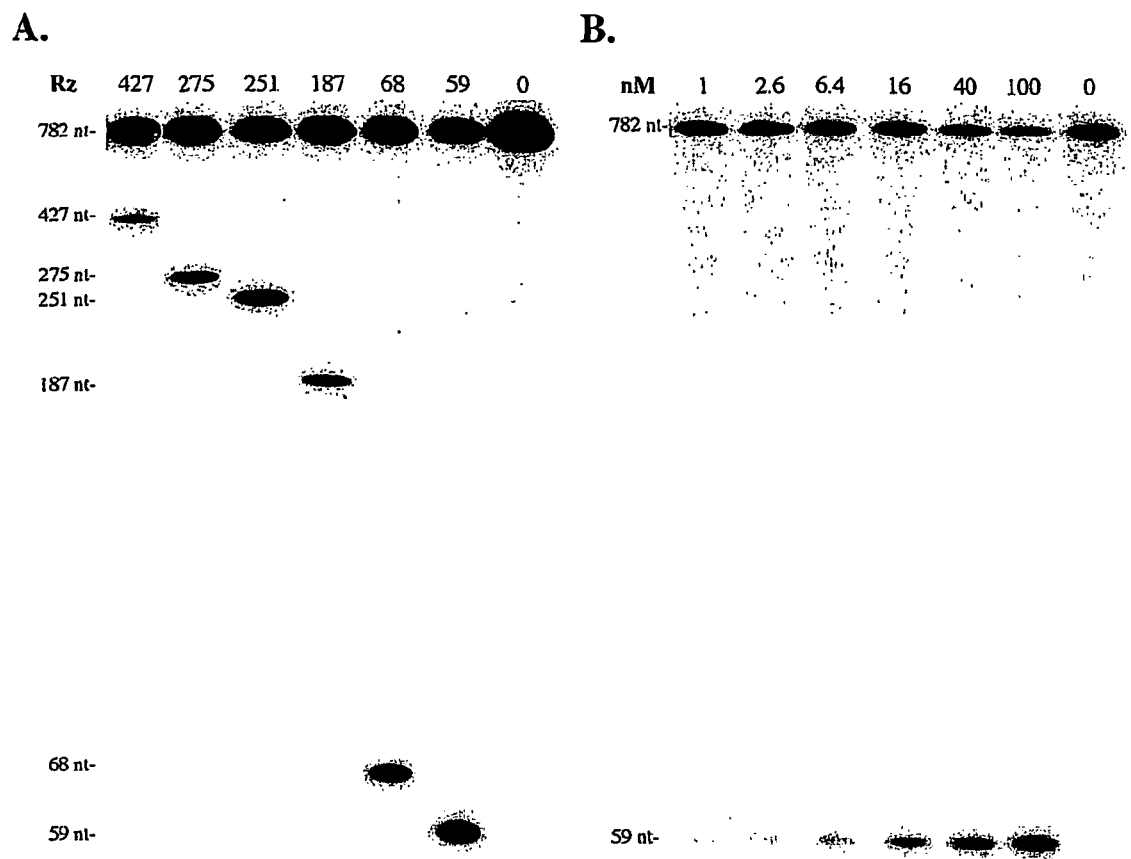
FIG. 6 contains two photographs of gels demonstrating in vitro cleavage of HPV16 E6/E7 RNA via Rz targeting library-selected sites. Panel A: 40 nM of the individual Rz and 10 nM of 5'-end $^{32}$P-labeled HPV16 target RNA (782 nucleotides) were incubated for 30 minutes at 37° C. in 20 mM Tris-HCl (pH 7.4) containing 25 mM $MgCl_2$. Panel B: 1, 2.6, 6.4, 16, 40, and 100 nM of Rz59 and 10 nM of 5'-end $^{32}$P-labeled HPV16 E6/E7 RNA (782 nucleotides) were incubated for 30 minutes at 37° C. in 20 mM Tris-HCl (pH 7.4) containing 25 mM $MgCl_2$.

The catalytic activities of sRz were determined using single turnover conditions. Briefly, 10 nM of 5'-$^{32}$P-labeled target RNA was incubated with 40 nM Rz in buffer containing varying concentrations of $MgCl_2$ (1, 5, or 25 mM) at 37° C. for 30 minutes. 25 mM $MgCl_2$ was used because it has been reported to yield cleavage rates similar to those observed in the presence of cytosol (Nedbal and Sczakiel, *Antisense Nucleic Acid Drug Dev.*, 7:585-9 (1997)). Cleavage products were then analyzed by denaturing PAGE (FIG. 6). Eight of 11 of the sRz targeted to HPV16 E6/E7 mRNA exhibited even greater activity than Rz427, the most active Rz identified using the LS1 oligonucleotide library procedure (Pan et al., *RNA*, 7:610-621 (2001)). Two others exhibited activity roughly comparable activity exhibited by Rz427. Nearly all of the sRz were "highly efficient" according to previous categorizations (Pan et al., *RNA*, 7:610-621 (2001)). The "highly efficient" category reflects cleavage of about 40 to 50% of target RNA after 30 minutes at 37° C. with 40 nM Rz concentration. With the higher concentrations of magnesium, sRz catalytic activities were increased, but the differential between them was decreased somewhat. For example, compared with Rz427, the best selected sRz (sRz59) was 2.4 times more active in 25 mM $MgCl_2$ and 4.5 times more active in 5 mM $MgCl_2$. In addition, only sRz59 and sRz68 exhibited demonstrable activity with 1 mM $MgCl_2$. Even when the concentration of sRz59 was reduced to 1 nM in reactions containing 10 nM of target, cleavage products were still visible after PAGE and autoradiography (FIG. 6B).

Analysis of the efficient cleavage sites for HPV16 E6/E7 target RNA revealed a tendency for a GUA-triplet, similar to that for other Rz, with GUU and GUC exhibiting slightly lower prevalence (Table 3). A distinguishing feature was two "D" nucleotides ("A", "G", or "U", but not "C") surrounding the triplet, yielding a consensus of 5'-DRUHD-3'. More extended analyses with other target RNAs yield a similar consensus of 5'-DNUHD-3', with the "N" being "G" nearly two thirds of the time.

TABLE 3

Analysis of nucleotide availability surrounding cleavage sites

| Position | 16.10 | 16.9 | 16.8 | 16.7 | 16.6 | 16.5 | 16.4 | 16.3 | 16.2 | 16.1 | 17 | 1.1 | 1.2 | 1.3 | 1.4 | 1.5 | 1.6 |
|---|---|---|---|---|---|---|---|---|---|---|---|---|---|---|---|---|---|
| Adenosine | 1 | 4 | 1 | 5 | 2 | 2 | 3 | 3 | 1 |  |  | 4 | 2 | 4 | 0 | 4 | 3 | 4 |
| Cytidine | 2 | 1 | 2 | 1 | 1 | 1 | 2 | 0 | 0 |  |  | 2 | 0 | 1 | 1 | 1 | 2 | 3 |
| Guanosine | 2 | 0 | 1 | 2 | 4 | 2 | 2 | 3 | 7 |  |  | 0 | 3 | 2 | 4 | 3 | 1 | 1 |
| Uridine | 3 | 3 | 4 | 0 | 1 | 3 | 1 | 2 | 0 | 8 |  | 2 | 3 | 1 | 3 | 0 | 2 | 0 |

Figure 7:
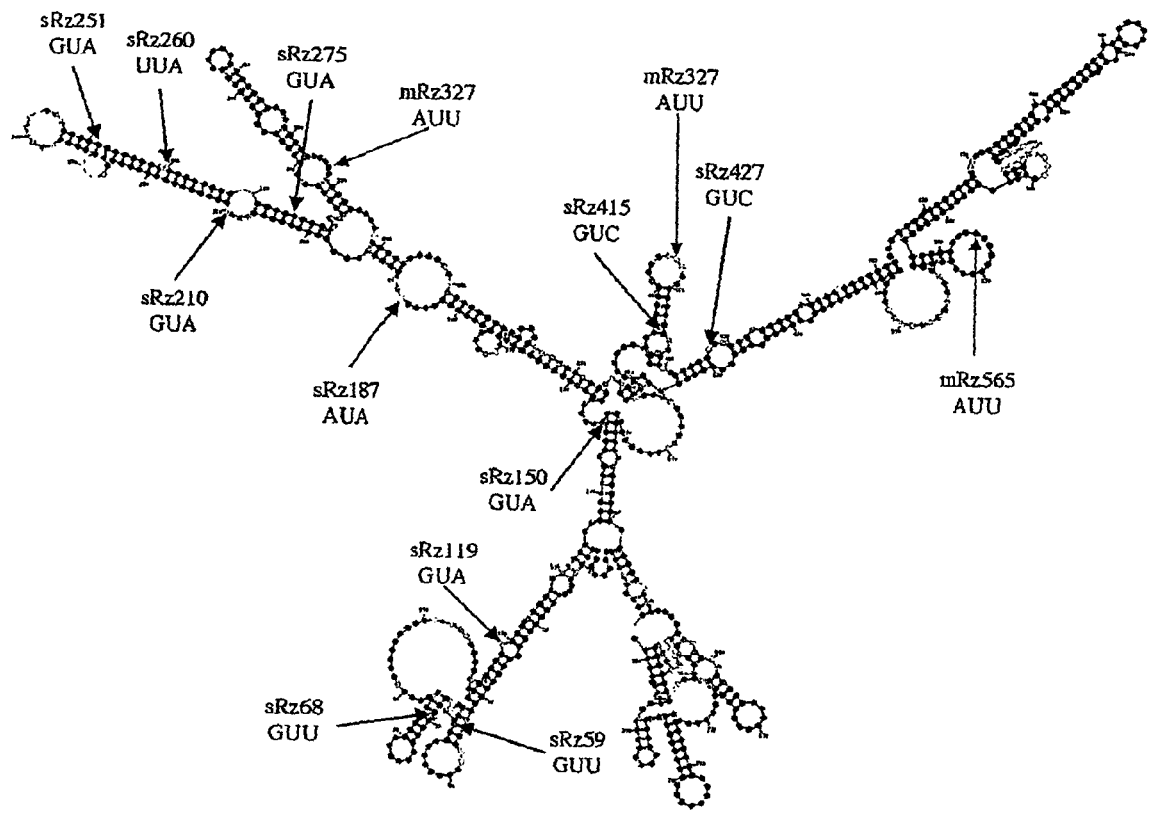
FIG. 7 is a schematic diagram of the predicted structure of HPV16 E6/E7 mRNA as determined using mFold plot. The locations of the Rz sites identified by library selection are labeled as sRz sites, and those chosen on the basis of the mFold modeling are labeled as mRz.

After identification of efficient cleavage sites in the various target RNAs, the nucleotides in positions surrounding the NUH triplet were compiled. "Position" indicates the nucleotide positions 3-10 in the complementary flanking sequence upstream of the NUH triplet in Helix III (16.x), and nucleotide positions 1-6 in the complementary flanking sequence downstream of the NUH triplet (1.x). Nucleotide positions are numbered as follows with the cleavage site being located between the underlined nucleotides (numbered 17 and 1.1):

(16.10------------------------------16.1)17(1.1------------------------------1.9)
5'-N N N N N N N N U <u>H N</u> N N N N N N N N-3' Target The HPV16 E6/E7 target RNA was modeled using the mFold program (FIG. 7; the locations of the sRz sites are denoted with arrows). In general, sRz sites are found at "transitions", where one flanking region is in a region predicted to be double-stranded, and the other flanking region is in a region predicted to be single-stranded. Surprisingly, sRz sites were rarely (if ever) found where the flanking sequences are predicted to both be in single-stranded regions (based on identification of about 50 sites in various targets). In fact, three Rz targeted to such sites in HPV16 E6/E7 RNA using mFold (mRz; FIG. 7) were constructed and found to be inactive (mRz406 and mRz565) or found to exhibit very low activity (mRz327).

For kinetic analyses, 40 nM Rz and 10-1000 nM of target RNA were incubated for various periods (ranging from 40 seconds to 60 minutes) to obtain kinetic data for both single and multiple turnover conditions. Results for the HPV16 E6/E7 targeted sRz generally revealed $K_m$'s of about 20 to 80 nM. sRz59 exhibited a $k_{cat}/K_m$ of $1.52\times10^7$ ($M^{-1}$ $min^{-1}$), a value about 5 times higher than Rz427's $k_{cat}/K_m$ value of $2.84\times10^6$ ($M^{-1}$ $min^{-1}$). This presumably reflects a faster chemical step of sRz59's catalytic activity, since $K_m$ values appear to be similar.

Example 10

Cell Culture Analysis of sRz Targeting HPV16 E6/E7 mRNA

The sRz targeted to HPV16 E6/E7 RNA were placed within the $SNIP_{AA}$ cassette as described herein. The HPV16-E6/E7 target construct and the $SNIP_{AA}$sRz constructs were co-transfected into 293T cells, and cultures were analyzed for the effects of sRz on HPV16-E6/E7 RNA expression. At 3 and 5 days after transfection with the $SNIP_{AA}$ constructs containing sRz (sRz59, sRz68, sRz187, sRz251, and sRz275) or with $SNIP_{AA}$-Rz427 (the most active Rz identified using the LS1 procedure), a substantial reduction of HPV16 E6/E7 RNA was observed (FIG. 8A). The largest reduction was produced by $SNIP_{AA}$-sRz59 at day 3. By day 5, the E6/E7 RNA transcripts were reduced by 75% in all of the sRz transfections, compared with co-transfections with the empty $SNIP_{AA}$ cassette.

In repeat co-transfection experiments, QPCR was used to measure HPV16 E6/E7 mRNA levels (FIG. 8B). All the $SNIP_{AA}$sRz constructs were very effective at reducing HPV16 E6/E7 target RNA levels, achieving reductions of about 60 to 80% on day 5. Essentially all reductions in HPV16 E6/E7 RNA levels were statistically significant at p<0.001. Statistically significant reductions were also evident on day 1 and day 7, with average decreases of 34% and 47%, respectively. This reductions shown in FIG. 8B were slightly greater than the reductions observed with similar $SNIP_{AA}$-Rz cassettes designed to express Rz targeting selected sites in HPV11 E6/E7 target RNA, but were smaller than the 90% reductions observed with $SNIP_{AA}$ constructs containing double ITRz. In contrast, parallel experiments with $SNIP_{AA}$ constructs containing catalytically inactive versions of Rz59 and Rz427 (mRz59 and mRz427) did not produce significant reductions in HPV16 E6/E7 RNA transcripts (FIG. 8C).

Growth experiments were conducted with SiHa cells (a human cell line derived from a cervical squamous cell carcinoma). SiHa cells contain an integrated copy of HPV16, and their growth is dependent, at least in part, upon continued expression of HPV16 E6/E7 transcripts (Rorke, J. Natl. Can. Inst., 89:1243-1246 (1997); Madrigal et al., Gyn. Onc., 64:18-25 (1997); and Tan and Ting, Cancer Res., 55:4599-4605 (1995)). While this protocol necessitates selection of growth-inhibited cells, it nevertheless provides a model system with sustained E6/E7 expression.

SiHa cells were transfected with the pCMV/BSD plasmids containing the various sRz in the $SNIP_{AA}$ cassette, and the transfected populations were selected for antibiotic resistance (with blastocidin S at 10 µg/mL). Selection was complete after 6 days. After 8 days, cells were counted in triplicate samples. Populations transfected with the 59, 68, or 251 $SNIP_{AA}$sRz constructs exhibited 40 to 45% reductions in cell growth (p<0.05), compared with cells transfected with the empty $SNIP_{AA}$ cassette or with a reporter expression construct. These reductions correspond to "maximal reductions" observed in other studies (Madrigal et al., Gyn. Onc., 64:18-25 (1997) and Tan and Ting, Cancer Res., 55:4599-4605 (1995)). It is possible that an 80% reduction in E6/E7 RNA expression levels still provides sufficient E6/E7 polypeptide to sustain growth at a 50% rate. It, however, also is possible that growth of SiHa cells is now only partially dependent upon E6/E7 expression. Cells transfected with the previously identified $SNIP_{AA}$-Rz427, and those transfected with the 187 or 275 $SNIP_{AA}$sRz constructs, exhibited more modest reductions (up to 15%) in growth rates. In repeat experiments, analysis of RNA by QPCR revealed equivalent reductions in HPV16 E6/E7 target RNA on day 5. In other experiments with $SNIP_{AA}$ constructs containing double ITRz, reductions of about 60 to 75% at days 7 and 12 were observed.

In summary, the LS2 library-screening procedure provides a relatively straightforward and rapid method for determining efficient cleavage sites in long, structured target RNAs. The iterative procedure was streamlined to 2 rounds of selection, and the entire procedure can be finished in a few days. A significant number of effective cut sites are generally identified. Most sRz identified are "highly efficient" in vitro. This in part reflects the fact that their activity within the library pool is considerably decreased by the presence of fixed 5'- and 3'-sequences, ensuring major increases in activity when they are constructed and tested without the extraneous flanking sequences. More importantly, the selected Rz targeted to HPV16 E6/E7 RNA were highly effective in cell culture models, and they can be used in in vivo models. These results demonstrate that the LS2 method is relatively simple, iterative Rz-library screening method that can be used to design hammerhead ribozymes.

Example 11

Analysis of Rz and Dz Specificities Targeted to Hepatitis B Virus (HBV) RNA

Various mutant Rz and Dz (mutants of $Rz885_{(HBV)}$ and $Dz879_{(HBV)}$; Pan et al., RNA, 7:610-621 (2001) and International Patent Application No. PCT/US01/46178) were tested to assess the affects of mutations on the ability of the Rz or Dz to interact with and cleave a target RNA. Mutant forms of $Rz885_{(HBV)}$ and $Dz879_{(HBV)}$ were synthesized and incubated with HBV RNA transcripts (Pan et al., RNA, 7:610-621 (2001)). The mutations were introduced into the N or Q regions of the Rz or Dz (FIG. 9A). The nucleotide numbering is set forth in FIG. 9A. To generate the mutants, a "G" was replaced with an "A"; an "A" was replaced with a "G"; a "C" was replaced with a "T" or "U"; and a "T" or "U" was replaced with a "C." Many mutations reduced the activity of the Rz and Dz (Table 4 and FIG. 9B). Some mutations increased the catalytic activity of the Rz and Dz (Table 4 and FIG. 9B).

TABLE 4

Relative activity for mutant Rz and Dz.

| Lane in FIG. 9B | Rz/Dz mutation | % Relative Activity of Rz | % Relative Activity of Dz |
|---|---|---|---|
| 1 | No Rz or Dz | 0 | 0 |
| 2 | Wild type | 100 | 100 |
| 3 | $N_1$ | 0 | 0 |
| 4 | $Q_1$ | 14 | 57 |
| 5 | $N_1 + Q_1$ | 0 | 1 |
| 6 | $N_2$ | 41 | 0 |
| 7 | $Q_2$ | 2 | 19 |
| 8 | $N_2 + Q_2$ | 7 | 0 |
| 9 | $N_{1+2}$ | 4 | 0 |
| 10 | $Q_{1+2}$ | 0 | 5 |
| 11 | $N_3$ | 110 | 11 |
| 12 | $Q_3$ | 38 | 17 |
| 13 | $N_3 + Q_3$ | 48 | 0 |
| 14 | $N_{2+3}$ | 0 | 0 |
| 15 | $Q_{2+3}$ | 1 | 0 |
| 16 | $N_4$ | 102 | 17 |
| 17 | $Q_4$ | 59 | 17 |
| 18 | $N_4 + Q_4$ | 64 | 0 |
| 19 | $N_{3+4}$ | 57 | 0 |
| 20 | $Q_{3+4}$ | 8 | 5 |
| 21 | $N_5$ | 88 | 110 |
| 22 | $Q_5$ | 77 | 20 |
| 23 | $N_5 + Q_5$ | 72 | 23 |
| 24 | $N_{4+5} + Q_{4+5}$ | 5 | 0 |

Example 12

Cell Culture Analysis of siRNA Targeting HPV16 E6/E7 mRNA

Constructs containing cassettes that express RNA molecules designed to induce RNA interference against HPV16 mRNA were made and tested in Flip293 cells as described elsewhere (U.S. Provisional Patent Application No. 60/449,066). In particular, the following cassettes were tested one day after transfection for the ability to reduce HPV16 mRNA levels within cells when driven by a CMV promoter sequence: p1CLIP$_S$/HPV16$_{C+50-68+GUU}$; p1CLIP$_{AS}$/HPV16$_{C+68-50+GUU}$; pSIR/HPV16si$_{C+50-68+GUU}$; p1CLIP$_{HP}$/HPV16$_{C+50-68+GUU}$; pSIR$_{HP}$/HPV16$_{C+50-68+GUU}$; p2CLIP$_{HP}$/HPV16$_{C+50-68+GUU}$; p2CHOP$_{HP}$/HPV16$_{C+50-68+GUU}$; pSNIP$_{HP}$/HPV16$_{C+50-68+GUU}$; p2CLIP$_{HR}$/HPV16$_{C+50-68+GUU}$; p2CHOP$_{HR}$/HPV16$_{C+50-68+GUU}$; pSNIP$_{HR}$/HPV16$_{c+50-68+GUU}$; and pSNIP (empty cassette). In addition, the following cassettes were tested two days after transfection for the ability to reduce HPV16 mRNA levels within cells when driven by a U6 promoter sequence: p1CLIP$_S$/HPV16$_{C+50-68+GUU}$; p1CLIP$_{AS}$/HPV16$_{C+68-50+GUU}$; pSIR/HPV16si$_{C+50-68+GUU}$; p1CLIP$_{HP}$/HPV16$_{C+50-68+GUU}$; pSIR$_{HP}$/HPV16$_{C+50-68+GUU}$; p2CLIP$_{HR}$/HPV16$_{C+50-68+GUU}$; p2CHOP$_{HR}$/HPV16$_{C+50-68+GUU}$; pSNIP$_{HR}$/HPV16$_{C+50-68+GUU}$; pSNIP cassette containing sRz59; and pSNIP (empty cassette).

Significant reductions in target mRNA were detected for cells containing the pSIR/HPV16si$_{C+50-68+GUU}$ cassette or the pSIR$_{HP}$/HPV16$_{C+50-68+GUU}$ cassette when the cassette was expressed from a CMV promoter sequence (FIG. 10A). A significant reduction in target mRNA also was detected for cells containing the pSIR/HPV16si$_{C+50-68+GUU}$ cassette, the pSIR$_{HP}$/HPV16$_{C+50-68+GUU}$ cassette, or the pSNIP$_{HR}$/HPV16$_{C+50-68+GUU}$ cassette when the cassettes were expressed from a U6 promoter sequence (FIG. 10B).

These results demonstrate that cassettes can be designed to express RNA sequences that induce RNA interference and reduce HPV16 mRNA levels within cells.

Example 13

Kinetic Analysis of Rz and Dz

The kinetics of Rz59$_{(HPV16\ E6/E7)}$, Dz57$_{(HPV16\ E6/E7)}$, and Dz589$_{(HPV16\ E6/E7)}$ were determined using HPV16 E6/E7 RNA as the target (Table 5). Rz59$_{(HPV16\ E6/E7)}$ and Dz57$_{(HPV16\ E6/E7)}$ target cleavage sites that were identified using the LS2 protocol, while Dz589$_{(HPV16\ E6/E7)}$ targets a cleavage site that was identified using the LS3 protocol. These results demonstrate that Rz and Dz can be designed to have high levels of catalytic activity. In addition, the measured $k_m$ values indicate that these Rz and Dz can function at a high level within cells.

TABLE 5

Kinetic analysis of Rz and Dz cleavage of target RNA.

| Rz/Dz | $k_m$ (nM) | $k_{cat}$ (min$^{-1}$) | $k_{cat}/k_m$ (M$^{-1}$·Min$^{-1}$) |
|---|---|---|---|
| Rz59 | 21.05 | 0.32 | $1.52 \times 10^7$ |
| Dz57 | 97.64 | 0.35 | $3.58 \times 10^6$ |
| Dz589 | 21.46 | 2.69 | $1.25 \times 10^8$ |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating HPV infection comprising administering an effective amount of a nucleic acid molecule to a patient in need thereof, wherein said nucleic acid molecule inhibits expression associated with HPV replication, wherein said nucleic acid molecule comprises double-stranded RNA or encodes a nucleic acid comprising double-stranded RNA, and wherein at least one strand of said double-stranded RNA comprises a sequence that is complementary to nucleotides 129 to 147 of SEQ ID NO:85.

2. The method of claim 1, wherein said nucleic acid molecule is administered topically.

3. The method of claim 2, wherein said nucleic acid molecule is administered topically to a portion of the genital organ of said patient.

4. The method of claim 2, wherein said nucleic acid molecule is administered topically to cervical tissue of said patient.

5. The method of claim 1, wherein said patient suffers from cervical intraepithelial dysplasia (CIN).

6. The method of claim 5, wherein said CIN is CIN I or mild dysplasia.

7. The method of claim 5, wherein said CIN is CIN II or moderate to marked dysplasia.

8. The method of claim 5, wherein said CIN is CIN III or severe dysplasia to carcinoma-in-situ.

9. The method of claim 8, wherein said carcinoma-in-situ is localized to the intraepithelial tissue or the superficial layer of the cervix.

10. A method for treating a mammal having cells infected with HPV, said method comprising administering a nucleic acid molecule to said mammal under conditions wherein the number of said cells infected with said HPV is reduced, wherein said nucleic acid molecule comprises a sequence complementary to nucleotides 129 to 147 of SEQ ID NO:85, wherein said nucleic acid comprises double-stranded RNA molecule or encodes a nucleic acid comprising double-stranded RNA.

11. The method of claim 10, wherein said mammal is a non-human, immunodeficient mammal, and wherein said cells are human cells.

12. The method of claim 10, wherein said mammal is a nude or SCID mouse.

13. The method of claim 10, wherein said mammal is a human.

14. The method of claim 10, wherein said cell is a skin cell or epithelial cell.

15. The method of claim 10, wherein said nucleic acid molecule is administered topically to said mammal.

16. The method of claim 15, wherein said nucleic acid molecule is administered topically to a portion of the genital organ of said mammal.

17. The method of claim 15, wherein said nucleic acid molecule is administered topically to cervical tissue of said mammal.

18. The method of claim 10, wherein the number of said cells infected with said HPV is reduced by at least 25 percent.

19. The method of claim 10, wherein the number of said cells infected with said HPV is reduced by at least 50 percent.

20. The method of claim 10, wherein the number of said cells infected with said HPV is reduced by at least 75 percent.

21. The method of claim 10, wherein said cells infected with said HPV contain non-integrated HPV nucleic acid.

22. The method of claim 10, wherein said cells infected with said HPV contain replicating HPV.

* * * * *

UNITED STATES PATENT AND TRADEMARK OFFICE
CERTIFICATE OF CORRECTION

PATENT NO. : 7,704,965 B2  Page 1 of 1
APPLICATION NO. : 10/519122
DATED : April 27, 2010
INVENTOR(S) : Gary A. Clawson It is certified that error appears in the above-identified patent and that said Letters Patent is hereby corrected as shown below:

Column 1, lines 19-21, please delete "Funding for the work described herein was provided by the federal government, which may have certain rights in the invention." and insert --This invention was made with government support under Grant No. AI85337, awarded by the NIH/NIAID. The Government has certain rights in the invention.-- therefor.

Signed and Sealed this

Twenty-fourth Day of August, 2010

David J. Kappos
*Director of the United States Patent and Trademark Office*